(12) United States Patent
Merchez et al.

(10) Patent No.: US 8,599,378 B2
(45) Date of Patent: Dec. 3, 2013

(54) DEVICE AND METHOD FOR MULTIPARAMETER MEASUREMENTS OF MICROPARTICLES IN A FLUID

(75) Inventors: Benoit Merchez, Combaillaux (FR); Sebastien Raimbault, Argelliers (FR); Philippe Nerin, Montpellier (FR); Alexandra Urankar, Saint Clement de Riviere (FR)

(73) Assignee: Horiba ABX SAS, Montpellier (FR)

( * ) Notice: Subject to any disclaimer, the term of this patent is extended or adjusted under 35 U.S.C. 154(b) by 0 days.

(21) Appl. No.: 13/575,132

(22) PCT Filed: Feb. 2, 2011

(86) PCT No.: PCT/FR2011/050202
§ 371 (c)(1),
(2), (4) Date: Jul. 25, 2012

(87) PCT Pub. No.: WO2011/098707
PCT Pub. Date: Aug. 18, 2011

(65) Prior Publication Data
US 2012/0296570 A1    Nov. 22, 2012

(30) Foreign Application Priority Data
Feb. 10, 2010  (FR) .................................... 10 50948

(51) Int. Cl.
*G01N 15/02* (2006.01)
(52) U.S. Cl.
USPC ........................................................ 356/335

(58) Field of Classification Search
USPC ............................................ 356/335, 336, 39
See application file for complete search history.

(56) References Cited

U.S. PATENT DOCUMENTS

| 5,194,909 A | 3/1993 | Tycko |
| 5,247,340 A | 9/1993 | Ogino |
| 5,506,673 A | 4/1996 | Kosaka et al. |
| 6,074,879 A | 6/2000 | Zelmanovic et al. |
| 2005/0074894 A1* | 4/2005 | Li et al. .......................... 436/63 |
| 2005/0151967 A1 | 7/2005 | Kusuzawa |

FOREIGN PATENT DOCUMENTS

WO    2006/053960    5/2006

* cited by examiner

*Primary Examiner* — Roy M Punnoose
(74) *Attorney, Agent, or Firm* — Clark & Brody

(57) ABSTRACT

The invention relates to a method of classifying and flow measuring the refringence of at least two populations of particles present in a fluid. The method uses a light source that has small coherence time, with a coherence length Lc<100 μm, that is used under extinction conditions at a center wavelength selected as a function of a range of volumes and of a range of refractive indices expected for the particles under consideration. The method uses a device that, together with the light source, forms a converging illuminating beam of aperture angle that is selected as a function of the range of volumes and the range of refractive indices expected for the particles under consideration at the selected center wavelength.

27 Claims, 18 Drawing Sheets

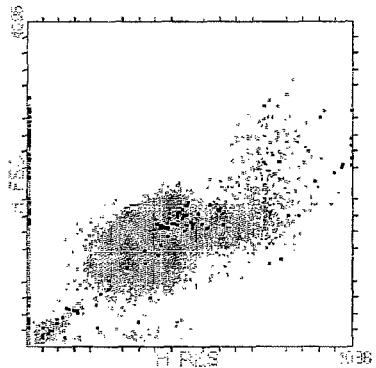 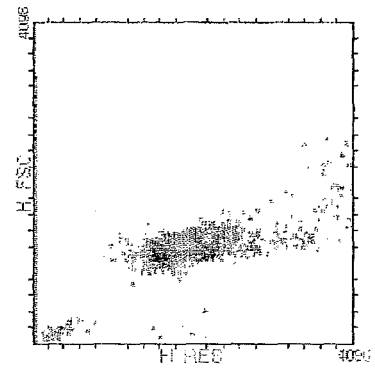
FIG.1A        FIG.1B
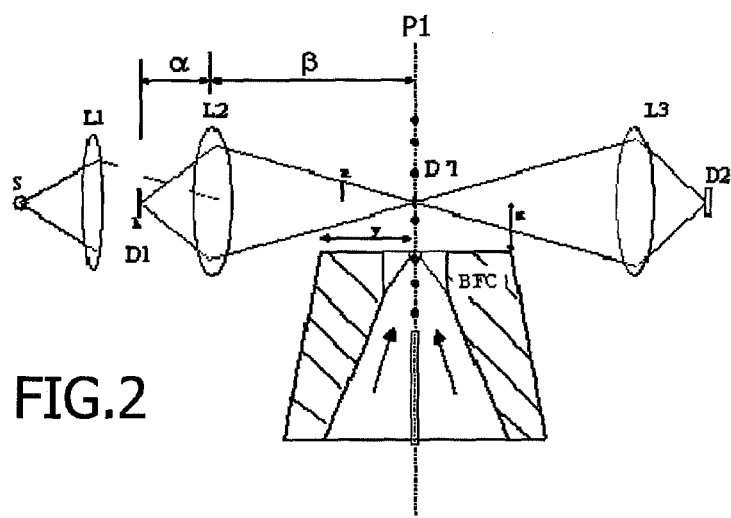
FIG.2
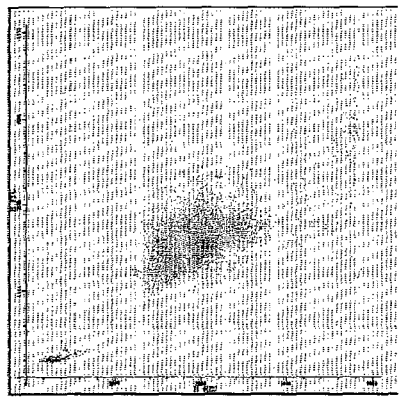 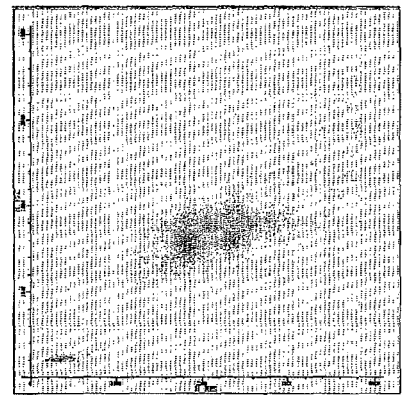
FIG.3A        FIG.3B

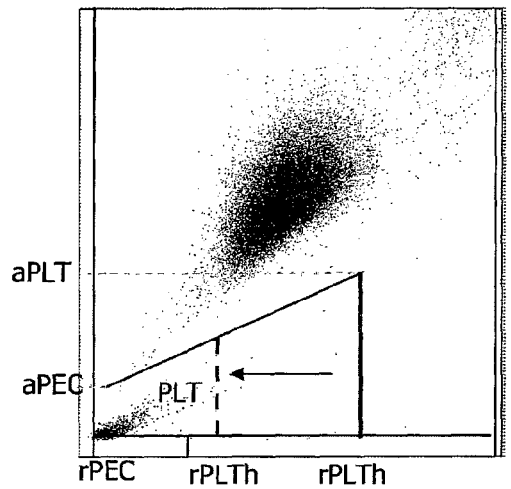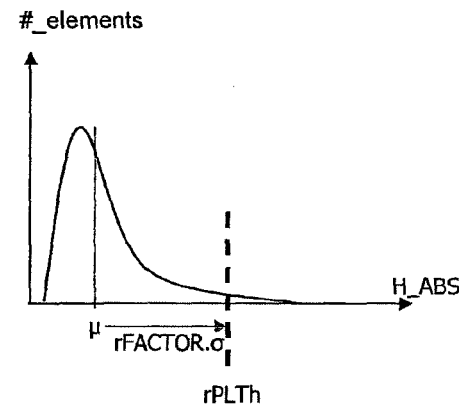
FIG.16A  FIG.16B
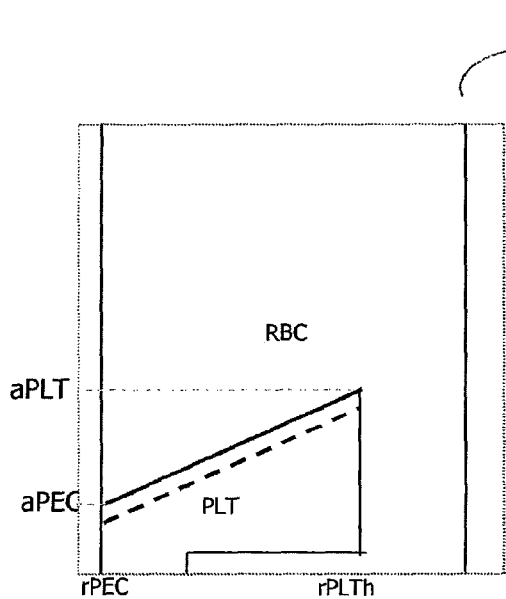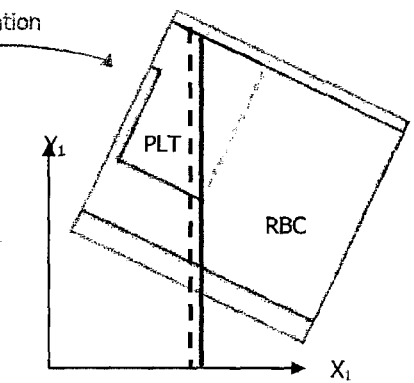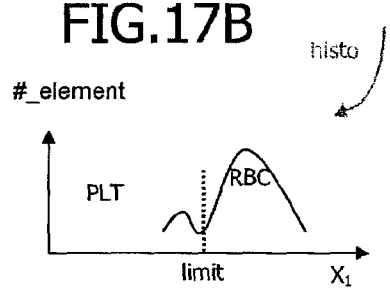
FIG.17A  FIG.17B  FIG.17C

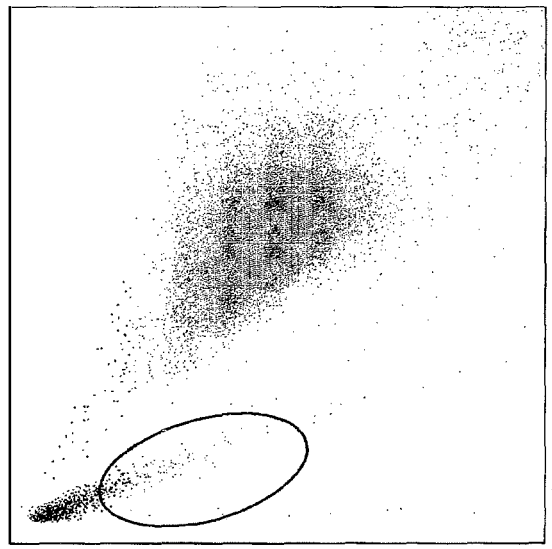
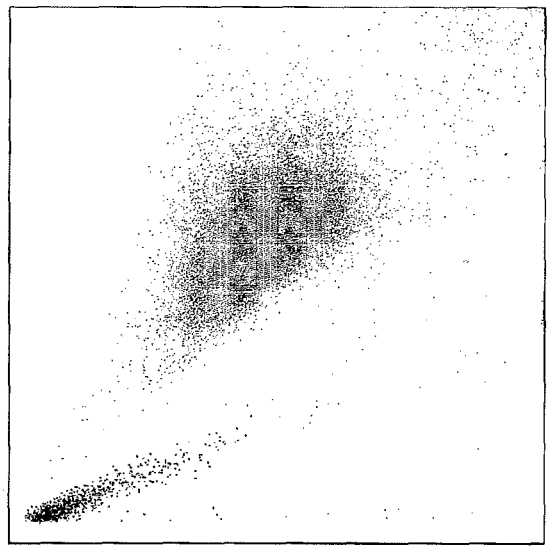
FIG.22A    FIG.22B
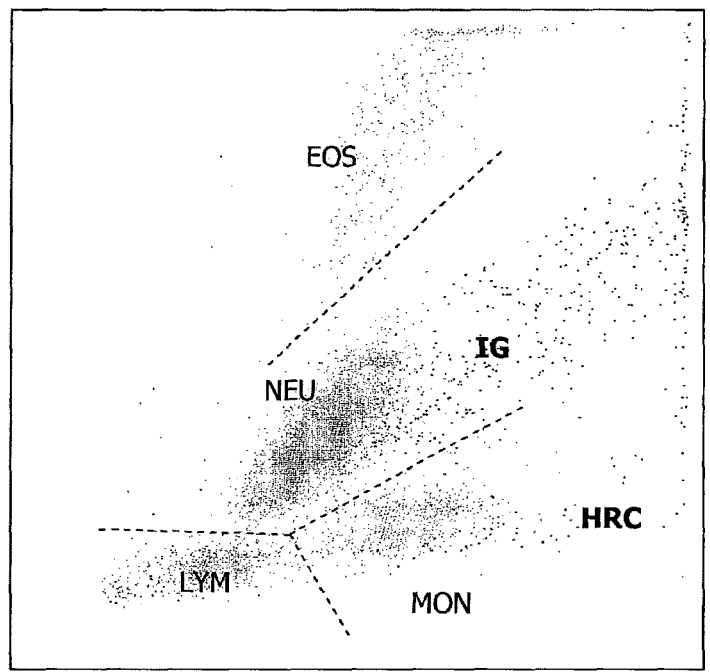
FIG.23

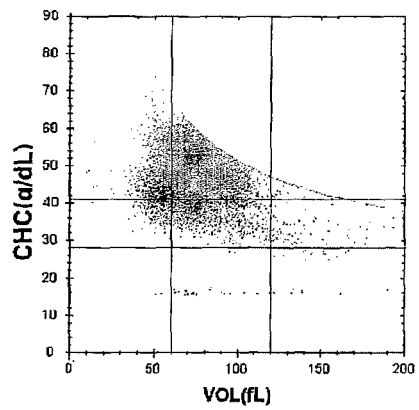 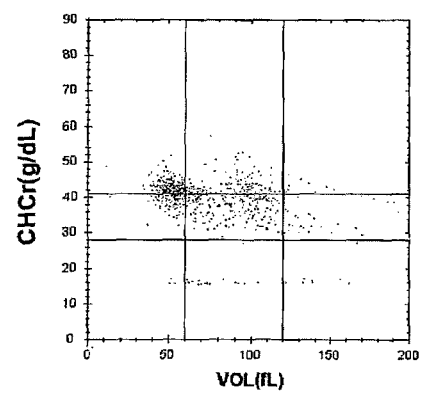
FIG.29A  FIG.29B
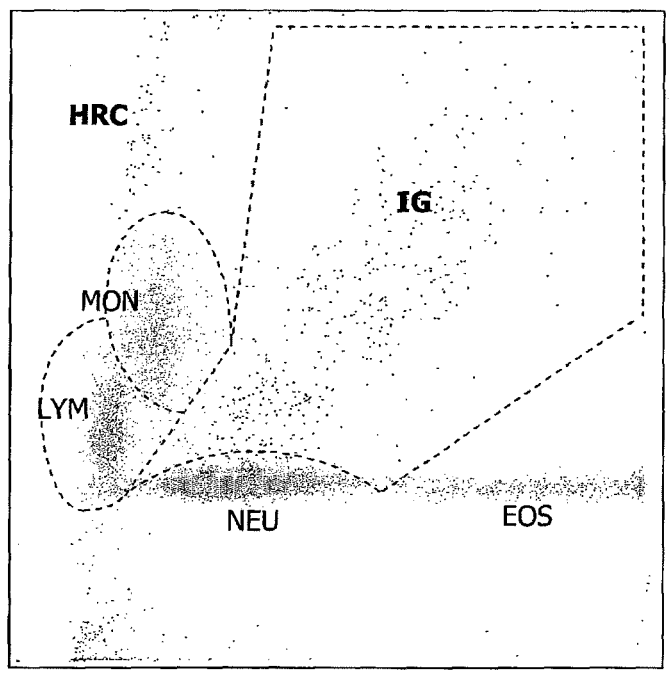
FIG.30

DEVICE AND METHOD FOR MULTIPARAMETER MEASUREMENTS OF MICROPARTICLES IN A FLUID

BACKGROUND OF THE INVENTION

The present invention relates to the general field of devices and methods for performing flow measurements to characterize microparticles, and in particular biological cells. The present invention relates more specifically to measuring the refringence of biological microparticles together with other parameters that are useful in biomedical applications.

In this context, most automatic cytology analyzers, such as hematology analyzers, are designed to measure cell characteristics that enable a laboratory physician to identify the origins of certain disorders. For example, diagnosing certain anemias, certain cancers, or following up certain medicinal treatments, are all performed by observing physical characteristics of each cell.

The object of the present invention is to develop a device and a method enabling each of the populations of particles contained in a biological sample, and in particular in blood, to be better distinguished and thus better counted. The invention also makes it possible to measure very accurately the intracellular hemoglobin content of each population of erythrocytes. By extension, the device and the method of the invention enable the populations of leukocytes in the sample to be better analyzed.

Concerning the erythrocyte cell line, the routine parameters provided by the most common analyzers are the following: the number of red blood cells per unit volume (#RBC), the mean cell volume (MCV, conventionally given in cubic micrometers ($\mu m^3$)), the red cell distribution index (or width) (RDW in %), the hematocrit level (HT in %), the mean hemoglobin concentration in the primary sample (HB), the mean corpuscular hemoglobin concentration (MCHC in grams per deciliter (g/dL)), and the mean corpuscular hemoglobin (MCH expressed in picograms (pg)).

Most hematology analyzers measure the parameters: #RBC, HB, and hematocrit level, with all of the other parameters being obtained by calculation.

Nevertheless, it should be observed that the most immature red blood cells, which contain residues of ribonucleic acid (RNA) and are known as "reticulocytes", can be measured using certain types of analyzer. A dye or fluorescent marker is then used as a stain to reveal the presence of intra-cytoplasmic RNA. The fraction of red blood cells that express a fluorescence or diffraction signal that is specific to RNA marking serves to determine the number of reticulocytes per unit volume (#RET).

In addition to these parameters, diagnosing certain anemias or tracking their treatment requires knowledge of the corpuscular hemoglobin concentration (CHC) of each red blood cell and/or of each reticulocyte (CHCr: corpuscular hemoglobin concentration of reticulocytes). Unlike the parameters MCHC and MCH, which are mean values calculated over an entire population of red blood cells, CHC and CHCr are values for the concentration of corpuscular hemoglobin in each blood cell and they are used to construct histograms showing the distribution of hemoglobin over populations of red blood cells and the immature fringe (the reticulocytes). For example, two patients having identical mean corpuscular hemoglobin concentrations may present statistical distributions that are very different over the red blood cells and the reticulocytes. That is well known in cytology. Thus, when a smear is examined using a microscope, the color of a red blood cell is strongly correlated to its hemoglobin content: the greater the concentration of hemoglobin, the greater the attenuation of light. That observation is a consequence of the Beer-Lambert law that shows that optical density is proportional to the concentration of the solute. Knowledge about the statistical distribution of hemoglobin within different cells provides information about the state of health of a patient. Departure from normality is a symptom to be interpreted by a laboratory physician. For example, red blood cells having a low hemoglobin content are said to be "hypochromic", while red blood cells having a high hemoglobin content are said to be "hyperchromic". When the hemoglobin distribution varies strongly from one red blood cell to another, that is a symptom of polychromatophilia. Cells for which the content is abnormal often present rheological properties that are abnormal and that give rise to other physiological symptoms, in particular with thalassemias or drepanocytoses. The hematological interpretation of these parameters on healthy subjects and patients is set out in the article published in Blood and entitled "Simultaneous measurement of reticulocytes and red blood cell indices in healthy subjects and patients with microcytic and macrocytic anemia", Onofrio et al., 1995, Vol. 85, pp. 818-823.

The hemoglobin content of reticulocytes is thus presently recognized as being a parameter that is very useful for diagnosing central anemias or indeed for following up the response of a patient to treatments. Furthermore, numerous publications in peer review journals and in numerous patent applications have been published over recent years, both about the clinical interpretation of hemoglobin distribution over all red blood cells, and about methods to be implemented in order to obtain that information.

For example, iron-deficiency anemias involve various fringes of the population, and in particular people under dialysis for whom an iron load balance is performed regularly. People suffering from hemorrhages or bleeding, people being treated by hemodialysis, or indeed people suffering from malnutrition, are liable to suffer from iron-deficiency anemias. Furthermore, subjects treated with erythropoietin (EPO) may develop an iron-deficient anemia syndrome even when their tissue reserves of iron are sufficient or even excessive, since the mechanism for synthesizing hemoglobin is limited by the deregulation of the iron fixing metabolism. Assays of ferritin and of the transferrin saturation coefficient are often used in diagnosing those biological disorders, but it is recognized that the serous concentration of those specific proteins is influenced by other factors in the event of inflammatory syndrome or infection.

The article entitled "Reticulocyte hemoglobin content (CHr): early indicator of iron deficiency and response to therapy" (Brugnara et al., Blood 1994, Vol. 83, pp. 3100-3101) teaches that the response to supplementary iron taken orally can be followed up by measuring the absolute count of reticulocytes and the corpuscular hemoglobin concentration. Thus, people who respond positively to that treatment benefit simultaneously from an increased number of reticulocytes and an increase in hemoglobin load from the first day. However, the mature red blood cell indices are not impacted until a very long time after the treatment, usually only after several weeks. Measuring #RET and the CHCr histogram is thus very important in determining in advance whether treatment is effective.

Thus, knowing the statistical distribution of the hemoglobin concentration over the red blood cell line, or indeed over a fraction thereof, is most advantageous in association with other more conventional parameters available from most hematology analyzers.

Concerning thrombocytes, it is most advantageous for the doctor or physician to be able to count and observe platelet activation, since that may represent an aggregation phenomenon that is at the origin of thromboses. This distinction between activated and non-activated platelets is relatively difficult to observe on a hematology analyzer.

The ability also to distinguish between platelets of large size (macroplatelets) and microcytes (which are red blood cells of very small size), is important in order to avoid making certain errors of diagnosis. Unfortunately, among hematology analyzers other than those based on lasers, there is at present no solution that is simple and effective for avoiding this potential confusion between macroplatelets and microcytes.

Concerning the leukocyte cell line, it is clear that accurately distinguishing between the various types of cell is a considerable advantage for enabling a laboratory physician to produce high-quality diagnoses. For example, the article "The cytoplasmic refractive index of lymphocytes, its significance, and its changes during active immunization (K. W. Keohane and W. F. Metcalf, Jan. 1, 1959, Experimental Physiology, 44, pp. 343-350) shows that measuring the refractive index of lymphocytes makes it possible to determine their level of activation after vaccination.

In order to measure the hemoglobin content of the red blood cell line, various methods based on flow cytometry have been proposed on the basis of optical measurements, mainly measurements of cell reflectivity or diffraction, such measurements being optionally combined with electrical measurements operating in continuous or pulsed manner via a measurement micro-orifice.

The first method of measuring corpuscular hemoglobin is attributed to D. H. Tycko. In U.S. Pat. No. 4,735,504, the author describes an optical method based on light diffraction measured in two regions of space that are identified by two parameters that correspond to very specific angles that are obtained by calculation. It should be observed that the red blood cell is previously treated chemically so as to give it a shape that is quasi-spherical. Within the limits of that approximation, it is possible to consider a red blood cell as being a uniform sphere of radius R and of refractive index IDX. Applying Mie theory to that simplified red blood cell model enables the intensity that is diffused in each region of three-dimensional space to be determined and enables an optimum configuration to be determined in which iso-concentration and iso-volume curves do not intersect, but on the contrary define a set of unambiguous curves. The set of curves makes it possible to solve the inverse problem consisting in determining the volume of the sphere and its refractive index on the basis of two measurements of the light diffracted in the two sub-pupils of the detection system.

The same author recognizes the complexity of that optical method in U.S. Pat. No. 5,194,909, column 4, lines 39 to 57. Instead of making two measurements of diffracted light, D. H. Tycko proposes measuring the volume of the cell by the conventional Wallace Coulter technique that consists in measuring the variation of impedance that results from a biological cell passing through a micro-orifice. That electrical measurement is associated with a measurement of light diffracted in a single pupil of the optical system. Once more, Tycko determines an annular pupil on the basis of two angles ($\theta_L$; $\theta_H$) that serves to define a set of curves giving a single solution for the hemoglobin content of the red blood cell on the basis solely of the measurement of the light diffracted in the pupil of the optical system.

Starting from the observation that calibrating the methods proposed by Tycko is very difficult to implement, since it is not possible to perform calibration with conventional latex beads, the Russian Novossibirsk team developed an original concept enabling the microparticle diffusion indicator to be measured. That system is referred to as a "scanning flow cytometer (SFC)". The angle between the light source, the microparticle, and the detector is a function of the movement of the microparticle in the fluid stream. Thus, the movement of the microparticle makes it possible to scan an angular sector that enables the diffractive light indicator to be recorded over a relatively large range of angles. Various members of that Russian team have applied an SFC to measuring the volume and the hemoglobin content of red blood cells.

In the article entitled "Calibration-free method to determine the size and hemoglobin concentration of individual red blood cells from light scattering" (Sem'yanov et al. Applied Optics, Vol. 39, No. 31, November 2000), the authors show that the diffraction pattern produced by red blood cells presents a series of maxima and minima. The positions and the amplitudes characteristics of those extrema are combined in order to lead to a calculation algorithm that enables the volume and the hemoglobin concentration of red blood cells to be deduced without performing a prior calibration operation.

In U.S. Pat. Nos. 5,817,519 and 6,025,201, it is necessary to use a laser in order to measure diffraction at small angles. The measurement is based on Mie theory and the principle that is used is thus similar to that used in the devices described by Tycko. Thus, in those documents, combining a diffraction measurement with acquiring another signal that may be an optical signal or an electrical single makes it possible to calculate the refringence of platelets only. Other cells cannot be distinguished by the electro-optical device that is described.

In US 2005/0134833 in the name of Beckman Coulter Inc., D. L. Kramer accepts that the methods based on measuring forward light diffraction suffer from error because they rely on cell refringence, which itself depends on the intra-cytoplasmic refractive index. He states that that refractive index may vary considerably as a function of solutes other than hemoglobin, in particular the presence of salts. He recommends a device based on a reflectivity measurement in order to avoid the inaccuracies of other systems. The operation of his device is applied to measuring red blood cell hemoglobin. The reflectivity measurement is combined with a cell volume measurement obtained by the technique based on variation in the impedance of a measurement micro-channel having a continuous current passing therethrough on the Coulter principle. Although the effectiveness of that device is not demonstrated, the author states that the reflectivity parameter is correlated with the hemoglobin content.

A non-optical approach is proposed in patent WO 97/26528 filed by the same company. In that patent, the corpuscular hemoglobin content is determined by performing two electrical measurements: one continuously and the other under pulsed conditions. Under continuous conditions, the outside volume of the cell is measured, whereas under pulsed conditions, the field interacts with the intra-cytoplasmic content that presents conductivity, which appears to be controlled by the concentration of hemoglobin.

It should also be observed that the above-mentioned inventions or publications relate only to measuring the hemoglobin content of red blood cells without any mention of reticulocytes.

In flow cytometry, it is possible to detect a reticulocyte only after specifically marking the ribonucleic acid as described for example in patent FR 2 759 166 filed by the Applicant. A study comparing various methods of detecting reticulocytes ("Reticulocyte enumeration: past & present", Riley et al., Laboratory Medicine, Vol. 32, No. 10, October 2001) finds in particular that fluorescent methods provide the best performance. More specifically, the thiazole orange compound is found to be one of the best markers of nucleic acids (DNA and RNA). The dominance of that molecule stems from that fact that it absorbs the incident light strongly and that the fluorescent yield is very high after hybridizing with nucleic acids. That method is proposed in all Horiba Medical analyzers for automatically counting reticulocytes ("Automated reticulocyte counting and immature reticulocyte fraction measurement", Lacombe et al., American Journal of Clinical Pathology, Vol. 112, No. 5, November 1999).

By way of example, U.S. Pat. No. 5,350,695 in the name of Miles Inc. describes a method of staining nucleic acids with oxazine 750 or with New Methylene Blue. Oxazine 750 causes nucleic acids to precipitate, thereby enabling them to be detected by an optical extinction measurement. The authors recognize that their invention relies on adapting an optical extinction measurement to the conventional above-described Tycko device. The absorption measurement is used exclusively for distinguishing immature cells, in particular reticulocytes, whereas the diffraction signals are used for calculating the globular indices constituted by the volume and the corpuscular hemoglobin content. In that patent, it is accepted that the absorption measurement needed for resolving immature cells is interdependent with the diffraction measurement. In order to reduce such interference, as described in example 3, columns 15 and 16, the authors propose a cell-to-cell correction method. Unfortunately, those calculations are complex and likely to be inaccurate since they need to decouple two optical phenomena of small amplitudes: firstly the refringence effect and secondly the absorption effect, those two effects being mixed together in the signal measuring optical extinction. A first limit on that correction method comes from the fact that the blood cell is assumed to be a perfect uniform sphere. Mie theory is used to calculate the proportion of the signal that is to be subtracted from the optical extinction signal. That calculation gives a new absorption value that can be attributed solely to the contribution of the dye and used to measure the quantity of nucleic acid and thus to determine the degree of maturity of the red blood cell.

FIG. 18 of document U.S. Pat. No. 5,350,695 compares the results of counting reticulocytes between the said method and the manual counting method. Although the correlation coefficient is not given, it can be seen that the measurements are highly dispersed and that the reticulocyte count is inaccurate below 2%. However, it is known that the mean lifetime of a red blood cell is 120 days: it can therefore be estimated that the red blood cell renewal rate is on average equal to 0.8% per day, which explains from a purely biological point of view the need to have a sensitive method that is capable of measuring well below 2%.

U.S. Pat. No. 5,360,739, still in the name of Miles Inc., describes a method of determining the corpuscular hemoglobin content that is based on Tycko's principle, i.e. light diffraction is measured at two diffraction angles respectively referred to as "red scatter low" and "red scatter high", whereas reticulocyte measurement is based not on measuring optical absorption as in U.S. Pat. No. 5,350,695, but on the principle of fluorescence. The authors envisage using two photo-excitable compounds, one in the red (oxazine 750) and the other in the blue (acridine orange and derivatives thereof). Under such circumstances, the authors propose coupling two lasers upstream from the vessel so that the light beams coincide at the measurement point. The proposed optical set-up uses illumination and detection axes that coincide, thereby introducing a considerable degree of complexity since, when using the compound that is photo-excitable in the blue, the set-up leads to making use of four measurement channels. In that method, an all-optical approach is preferred for determining the parameters of interest (volume and corpuscular hemoglobin concentration) of each red blood cell and of each reticulocyte contained in a blood sample.

U.S. Pat. No. 6,630,990 in the name of Abbott addresses the problem of measuring corpuscular hemoglobin concentration in a manner that is substantially equivalent to the above-described method. That patent presents an optical device enabling a plurality of cell lines to be resolved, in particular white blood cell lines and red blood cell lines. The system has a single light source and a single receiver presenting three measurement zones that define a singular configuration for using Mie theory to calculate the corpuscular hemoglobin and the cell volume. The main characteristics rely on using three diffraction angles for calculating the volume parameter V and the corpuscular hemoglobin HC, thereby leading to considerable complexity from a technological point of view, since a specific detector is necessary and the data is processed by a method operating in three-dimensional or four-dimensional space if fluorescence is added as a parameter for measuring the maturity of red blood cells. The complexity of the method of calibrating the device is also an important question that is not addressed in that document.

The parameter RET-y has been proposed by Sysmex for the XE2100 analyzer. Various experimental studies have been carried out by several teams in order to evaluate the clinical advantages of this RET-y parameter. For example, the article "New red cell parameters on the Sysmex XE-2100 as potential markers of functional iron deficiency" (Briggs et al., 2001, Sysmex Journal International, Vol. 11, No. 2) shows that the parameter RET-y is correlated with the hemoglobin content of reticulocytes. That parameter, which is the mean value of the forward scatter (FSC) restricted to the reticulocyte population only is calculated from the two-parameter FSC×FLUO representation of a sample of cells analyzed by flow cytometry in which, conventionally, the parameter FSC corresponds to the diffraction at small angles and the parameter FLUO corresponds to the fluorescence of a polymethine that is photo-excitable in the red and that is used for marking and quantifying nucleic acids (DNA/RNA). More recently, in the article "Potential utility of Ret-Y in the diagnosis of iron-restricted erythropoiesis" (Franck et al., Clinical Chemistry 50: pp. 1240-1242, 2004) C. Briggs et al. describe similar results. The authors recognize that the parameters MCH and CHr are correlated with the parameter RET-y. A nonlinear regression method is also proposed that enables the Sysmex XE2100 analyzer to be calibrated with the reference Advia 120 analyzer under the Bayer trademark. Those results are described and set out in patent EP 1 967 840 A2 filed by Sysmex in March 2007. Unfortunately, the non-linearities of the response of the FSC can lead to considerable inaccuracy, in particular for high values of the parameter CHr. In particular, for values close to 40 pg, it can be seen that the method is not sensitive since RET-y varies very little around that value. Furthermore, that patent makes reference only to reticulocyte populations, the FSX×FLUO two-parameter representation not being adapted to measuring other particles in circulating blood, in particular leukocytes.

Measuring diffraction at small angles, as described in the prior art patents, e.g. the Tycko device and set-ups derived therefrom, takes place through an annular pupil of apparent diameter lying in the range 5° to 15°. In order to measure diffraction at small angles with a good signal-to-noise ratio, those set-ups make use of a laser. Under such operating conditions, the numerical aperture of the illuminating beam is substantially zero. From a practical point of view, using a laser is the only solution that makes it possible, with a numerical aperture that is substantially zero, to produce the radiation at high power (several milliwatts) needed for effective measurement of diffraction at small angles.

Devices based on the measurement principles described in the prior art are therefore expensive because they include a laser.

Furthermore, they require the use of a stopper for stopping the laser beam in effective manner. Since the stopper needs to be aligned with great accuracy in order to avoid saturating the detector, it is particularly difficult to fabricate and adjust devices operating on that principle.

Furthermore, prior art devices are very sensitive to the quality of the sphering of the blood cells by the reagent. In devices operating with diffraction at small angles, the diffraction phenomenon corresponds substantially to that of a plane wave, which, by definition, presents zero divergence. The nature of that interaction with a microparticle is very sensitive to the effects of the shape of the microparticle. Furthermore, when a microparticle is not a perfect sphere, the result of the measurement includes significant errors. This has been found experimentally, as shown in FIGS. 1A and 1B. These are two-parameter plots of volume (RES) and laser diffraction (FSC) parameters concerning red blood cells measured over angles in the range 1° to 30°. FIG. 1A was obtained with a diluant from the supplier ABX (patent FR 2 759 166—Fluored®) that possesses a weak sphering index, whereas FIG. 1B was obtained using the same system but with a reagent that possesses a high sphering index (the Bayer diluant used on the Advia 2120). It can be seen that FIG. 1A includes significant errors since the set of populations are highly dispersed. In contrast, in FIG. 1B, the populations of particles are situated in a region of the plane that defines a set that is more compact with a high degree of FSC×RES correlation as shown by the elliptical shape of the set.

It is therefore clear that, independently of the measurement system, the nature of the reagent has a considerable influence on the result in prior art devices.

OBJECT AND SUMMARY OF THE INVENTION

A main object of the present invention is thus to mitigate such drawbacks by proposing a method of classifying and of flow measuring the refringence of at least two populations of cell particles present in a fluid by using a light source of short coherence time, of coherence length Lc<100 micrometers (μm), used under extinction conditions at a center wavelength selected as a function of the range of volumes and the range of refractive indices expected for the particles under consideration, the method comprising the steps of:

using the light source to form a converging illuminating beam of aperture angle lying in the range 1° to 60°, preferably 10° to 60°, selected as a function of the range of volumes and the range of refractive indices expected for the particles under consideration at the selected center wavelength and presenting lighting uniformity better than 10% in a rectangular volume measuring a×b×c, where a×b is the rectangular section of the beam having an aspect ratio a/b of less than 4, and where c is the depth of field defined as being the range of distances about the measurement point for which the power varies by no more than 10%, its value being situated at about 500 μm±250 μm;

causing the fluid with particles to flow through a measurement orifice;

measuring impedance vibrations (RES) as the particles go through the measurement orifice;

causing the biological solution to flow in the measurement window illuminated by the beam placed at the outlet from the measurement orifice;

measuring extinctions (EXT) on the axis of the beam as the particles pass through the measurement window, the measurement being performed by means of a device or a detector having a reception beam of aperture angle lying in the range 1° to 60° selected as a function of the range of volumes and the range of refractive indices expected for the particle populations under consideration;

merging the RES and EXT data to form events therefrom;

evaluating a relative refractive index IDX for each event using an expression of the type:

$$IDX = \frac{EXT - B \cdot \ln(RES + T) - D}{A \cdot \ln(RES + T) + C}$$

with A, B, C, D, and T being coefficients that depend on the measurement cycle; and classifying all of the events using at least one parameter selected from RES, EXT, and IDX.

The invention may be extended by adding fluorescence measurement in order to distinguish between various stages of cell maturity.

As shown in FIG. 2, the invention thus proposes a method making use of electro-optical means that are simple and that enable the refractive indices (or the refringences) of several cell lines to be measured. The appropriate reagents are selected when preparing the samples on which the measurements are to be performed using the method of the invention.

The originality of the invention lies in making use simultaneously of a volume measurement performed by the electrical method and of an optical extinction measurement in order to obtain particle refringence information.

It should be observed that particle refringence is a measurement relating to the refringence of the liquid medium in which the particle is immersed, and finally that the particle refringence measurement depends on parameters that characterize the measuring device.

Thus, the refringence of the particle or its refractive index, written m, may be expressed by the ratio of two physical magnitudes:

$$m = Ne/N_L$$

where, in given experimental conditions, Ne is the refractive index of the particle, and $N_L$ is the refractive index of the liquid medium in which the particle is immersed, this relative index also being written IDX below herein.

In cytological analysis, in particular in the field of hematology, this refringence information makes it possible, for example, to obtain improved classification of the cell populations under consideration, or may provide information about cell metabolism since it provides additional information about cell content or about the properties of its membrane.

In the method of the invention, no diffraction measurement of the kind is performed in order to evaluate refringence. The invention is based on using a measurement of optical extinction. Thus, the optical signal is measured against a light background and not a dark background as with prior art devices. One immediate consequence is that there is no need to use a laser, where lasers remain components that are relatively expensive and that remain more complex to use than non-laser sources.

The method of the invention thus makes use of a non-laser source that may for example be a semiconductor lamp such as a light-emitting, diode (LED), a super-luminescent LED, or indeed an incandescent lamp.

In the invention, the optical set-up is simpler than in prior art devices. In addition, implementation is easier, in particular since the measurement is performed against a light background so there is no need to stop the illuminating beam before the photo-electric detection step.

The use in the invention of an illuminating beam that converges with an aperture angle that is relatively large, greater than 10 degrees, serves to provide reduced sensitivity to the shape of the red blood cell.

It is known that a non-coherent converging beam may be resolved as a spectrum of plane waves having a variety of angles of incidence relative to the red blood cell.

The aperture angle of the illuminating beam is defined by the difference between these two values.

According to a preferred characteristic, this aperture angle lies in the range 10° to 60°.

Thus, unlike prior art devices, the particle is illuminated by a continuous spectrum of plane waves. Each wave then produces a diffraction pattern, such that the measured signal is the integrated response of all of the plane waves with the analyzed particle.

Since each of the plane waves sees the particle at a different angle, shape anisotropies are "averaged out".

This explains the superiority of the method of the invention over prior art devices when faced with particle shape conditions, in particular particle sphering. In particular with red blood cells, this prior step is obtained by chemical treatment of the microparticle, e.g. of the kind described by Y. R. Kima and L. Ornstein in the article "Isovolumetric sphering of erythrocytes for more accurate and precise cell volume measurement by flow cytometry" (Cytometry, 1983, Vol. 3, Issue 6, pp. 419-427).

The optical set-up of the invention is more tolerant as to the spherical quality of biological particles such as red blood cells. Thus, the requirements on the reagents in terms of sphering ability are reduced. Since sphering of the particle is no longer a factor that is totally decisive for implementing the measurement method, the invention makes it possible to enhance or to create other chemical functions, such as making the membrane permeable, as is needed for staining or marking specific structures inside the particle.

The invention thus makes it possible to sort the particles being analyzed into classes by measuring both impedance and extinction, on the basis of measuring their actual refringences and their volumes.

This makes it possible not only to determine a number of classes distinguished as a function of refringence, but also the fractions as a percentage of particles in each class, such that the sum of the fractions amounts to 100%.

In a particular implementation of the invention, as shown in FIG. 27, merely by adding a dichroic mirror F1 in the reception system together with a laser at 90° to the axis of the source S1, the optical set-up of the invention also makes it possible to measure fluorescence and thus to distinguish between erythrocytes and reticulocytes.

In the same manner, the device can enable the fluorescence of white blood cells to be measured and thus enable them to be separated as a function of the fluorescence response.

In particular, the invention provides solutions having better performance than previously published solutions and that are simpler.

An application of the method lies in measuring the refringence of red blood cells and of platelets. Knowing the refringent power of a red blood cell makes it possible to determine its hemoglobin concentration.

More generally, the invention makes it possible to determine the hemoglobin content of erythrocytes and of reticulocytes, to improve the classification of platelets compared with other cells or microparticles contained in a sample of whole blood (in particular red blood cells and background noise conveyed by the various fluids used for diluting the initial sample), and to determine the activation level of the platelets. The method of the invention may then be extended to all of the cells in circulating blood in order to classify and/or qualify white blood cells (in particular lymphocytes, monocytes, neutrophils, eosinopils, and basophils, and other nucleated cells).

According to an advantageous characteristic, the relative refractive index is calculated using an expression of the type:

$$IDX = \frac{EXT - B \cdot \ln(RES + T) - D}{A \cdot \ln(RES + T) + C}$$

with A, B, C, D, and T being coefficients that depend on the measurement cycle.

This characteristic enables the refractive index to be calculated quickly and simply, since it is an expression modeling the refractive index from two variables and a simple logarithmic function.

Advantageously, the analyzed particles are cells in a biological liquid.

Also, according to a preferred characteristic of the invention, the wavelengths used for measuring particle refringence lie in the red and the near infrared beyond 0.6 μm.

The range over which microparticle volumes are measured lies mainly from 0 to 500 femtoliters (fL). This applies in particular for red and white blood cells, and also for platelets.

With red blood cells, the selected range of wavelengths ensures the uniqueness of the solution, giving a hemoglobin concentration that is proportional to the refringence of each cell, itself determined by the optical extinction and impedance measurements.

According to an advantageous characteristic of the invention, the step of classifying events separates erythrocytes and platelets by using a wavelength lying in the range 600 nanometers (nm) to 800 nm and a numerical aperture NA1=NA2 lying in the range 0.2 to 0.6. This separation step is performed as a function of thresholds that define a belonging zone for platelets, the thresholds having values by default and being capable of being adjusted automatically.

This characteristic makes it possible to have a separation threshold that is appropriate for the sample being observed. In the invention, the optical extinction signal is measured and associated with the resistive signal in order to constitute an event. When certain particles are not seen in extinction, the method of the invention associates them with zero extinction. This sub-step processes these events solely on the basis of their impedance values.

Advantageously, the step of classifying events includes a sub-step of adjusting a resistive separation threshold between the particles for which extinction could not be measured, by determining a valley in a histogram prepared from all of the particles encountered.

According to a particular characteristic of the invention, the step of classifying events includes a sub-step of adjusting a resistive separation threshold calculated from statistical parameters, the mean and the standard deviation, of the particles encountered beneath a separation threshold defined by an affine straight line that is a function of the volume and of the optical extinction.

Under these circumstances also, the position of the separation threshold is determined as a function of the sample. This constitutes an original approach, since most present appliances that classify red blood cells (RBC) and platelets (PLT) do so on the basis of their volumes only. This threshold thus makes it possible to classify platelets that are of microcyte size, which cannot be done with other appliances in which microcyte interference is observed. Nevertheless, there are appliances in existence that make use of a diffraction measurement with a laser, but the method implemented is more complex than that of the present invention.

According to another particular characteristic of the invention, the step of classifying events includes a sub-step of adjusting a threshold defined by an affine straight line that is a function of the volume and (optical) extinction measurements after rotating the entire impedance (volume)/extinction plane so as to place a separation line vertically by determining a valley in a histogram made from the abscissa axis points of events situated on either side of said separation line.

Once more, the position of the separation threshold is determined as a function of the sample. The invention thus makes it possible to distinguish between, and therefore to classify, platelets and red blood cells of small size.

According to an advantageous characteristic of the invention, the method includes a step of calculating the corpuscular hemoglobin concentrations of particles classified as being in the erythrocyte population with the help of an affine expression that is a function of their refractive indices IDX.

The invention thus makes it easy to calculate corpuscular hemoglobin by using the known link between corpuscular hemoglobin and refractive index IDX.

Advantageously, the method includes a sub-classification step of classifying hypochromic, hyperchromic, and normochromic erythrocyte populations and microcyte, macrocyte, and normocyte erythrocyte populations.

Insofar as these populations differ by differences in volume and refringence, the measurements made using the invention serve to distinguish between microcyte, macrocyte, hypochromic, or hyperchromic populations that are defined and configured prior to classification as a function of the volume and of the hemoglobin content. The way the differences between these populations are defined are often specific to each laboratory. Nevertheless, a setting by default may be offered.

According to an advantageous characteristic of the invention, the method includes a step of calculating the densities of the particles classified in the platelet population using an affine expression that is a function of their refractive indices.

The invention makes it easy to evaluate the density of platelets by the relationship, known from elsewhere, between density and refractive index.

Advantageously, the method further includes a step of calculating the dry weights of platelets from their densities and from their volumes as known by the impedance measurements.

This step makes it possible to have access to a magnitude that is meaningful and important from a biological point of view: the quantity of granules of the platelet. These granules are expelled when the platelet becomes activated. Thus, platelet density reveals platelet activation. A set of platelets that have been activated contain few or no granules. Measuring the refractive index thus serves indirectly to measure their degree of activation. It is emphasized here that the measurement of particle refractive index is relative to the medium in which the particle is immersed, and also relative to the structure specific to the particle. Thus, the interpretation of platelet refringence measurements also relates to their internal complexity: a platelet containing small granules of high refringence will have an apparent refractive index that is greater than the same platelet that has lost its granules while being activated. Finally, the calculated refractive index is that of a uniform sphere of volume equal to the volume of the microparticle that would have produced optical extinction identical to the particle being analyzed (platelet, granulocyte, etc. . . . ).

According to a particular characteristic, the method of the invention includes a sub-classification step of classifying normal platelets, activated platelets, microplatelets, and macroplatelets. Since the concept of a "macroplatelet" relates to volume, the sub-classification may be adapted for each laboratory, as with erythrocytes.

According to an advantageous characteristic, the step of classifying events separates populations of leukocytes as constituted in particular by lymphocytes, monocytes, granulocytes, neutrophils, and eosinophilic granulocytes, and comprises the steps of:

a) using a first two-dimensional (2D) thresholding sub-step (REX×EXT or VOL×IDX) to separate background noise corresponding to the presence of debris, platelet aggregates, erythroblasts, artifacts, etc.; and b) using successive 2D thresholding sub-steps to separate the various populations and their atypical or immature subpopulations, and including:
  i) a sub-step of automatically adjusting a threshold between lymphocytes and neutrophilic granulocytes;
  ii) a sub-step of automatically adjusting a threshold between neutrophilic and eosinophilic granulocytes; and
  iii) a sub-step of automatically adjusting a threshold between monocytes and neutrophilic granulocytes.

The refractive index (IDX) transformation made possible by the invention gives access to information, that is more accurate and more orthogonal. It makes it possible to eliminate the component that, in optical extinction, is correlated to volume. Thus, 2D thresholding is advantageously performed on the magnitudes calculated from the volume (VOL) and from the refractive index (IDX), instead of on the impedance parameter (RES) and the extinction parameter (EXT) proper. As mentioned above, the statistical refringence properties provide more accurate information than does the optical extinction.

Thereafter, the information is interpreted differently for each population and it is therefore necessary to classify the population. For example, activation may be evaluated for lymphocytes, granulation for neutrophil or eosinophil granulocytes, etc.

Advantageously, the method includes a step of calculating an activation index for particles classified as lymphocytes with the help of an affine expression that is a function of the calculated relative refractive index.

By way of example, the refractive index variations of lymphocytes are described in the document entitled "The cytoplasmic refractive index of lymphocytes, its significance and its changes during active immunization" (Metcalf et al., Experimental Physiology, 44, pp. 343-350, 1959) and in the document "Changes in blood lymphocyte cytoplasmic refractive index following skin grafting in rabbits" (Metcalf et al., Blood 1972-39: pp. 113-116).

The invention makes it possible to evaluate lymphocyte activation by using the relationship known from elsewhere between said activation and the calculated relative refractive index.

According to an advantageous characteristic of the invention, the method includes a step of calculating an activation index for particles classified as lymphocytes by analyzing the 2D distribution of volumes and of optical extinctions, and by determining a statistical ellipse surrounding the population of lymphocytes, the ellipse being defined by the position of its center, by its major axis, by its minor axis, and by its angle.

The ability to determine an ellipse that surrounds the lymphocytes by using the volume and the refractive index information is likewise made possible by means of the invention. Furthermore, in the VOL×IDX plane, the 2D statistical properties give access to additional information that is more accurate since it is not correlated with volume.

According to a particular characteristic, the method of the invention includes a step of calculating a lobularity/granularity index for the particles classified as neutrophilic granulocytes with the help of an affine expression that is a function of the calculated relative refractive index IDX.

The invention makes it easy to evaluate the lobularity/granularity of neutrophilic granulocytes because of the relationship between such lobularity/granularity and the calculated relative refringence.

According to an advantageous characteristic of the invention, the method includes a step of calculating a lobularity/granularity index for the particles classified as neutrophilic granulocytes by analyzing the 2D distribution (resistive and extinction) or (volume and refractive index) measurements, and by determining a statistical ellipse surrounding the population of neutrophilic granulocytes, the ellipse being defined by the position of its center, by its major axis, by its minor axis, and by its angle.

This step makes it possible to obtain a mean index.

According to a particular characteristic, the step of classifying events separates basophilic granulocytes from other leukocyte populations and comprises the steps of:

a) using 2D thresholding to separate the background noise corresponding to the presence of erythrocyte debris, platelet aggregates, erythroblasts, artifacts, etc.; and b) separating basophilic granulocytes from other leukocytes by 2D thresholding, including automatic adjustment of a threshold between the basophilic granulocytes and the other leukocytes.

The term "2D thresholding" is used to mean thresholding in the RES×EXT, VOL×IDX planes or in the plane of any combination of the available magnitudes. Classification is possible after any transformation that conserves order relationships.

Before proceeding with measurement and classification, the sample in question is treated with a particular reagent (e.g. the ABX Basolyse reagent from the supplier Horiba Medical) that preserves the nucleus-cytoplasm ratio of basophils. The automatic positioning method may be performed by thresholding in an RES×EXT plane, and consists in analyzing the distribution of other leukocytes that have "shrunk" around their nucleuses. Starting from the center and the standard deviation, a threshold is then placed above the "shrunken" leukocytes. The other thresholds are fixed. With other forms of windowing and with other methods of adjustment, the method of the invention makes it possible to do the same in the VOL×IDX plane.

Advantageously, the method of the invention includes a step of detecting events presenting an abnormal relative refractive index and corresponding in fact to interference due to the presence of lipemia, crystals, bubbles, etc.

Such a step serves to detect the quality of the sample and thus of the measurements that have been performed thereon.

According to an advantageous characteristic, the method includes a step of detecting events having an abnormal relative refractive index and a volume distribution that is typical of an emulsion. The events that are then detected constitute interference. The invention thus enables them to be detected.

According to an advantageous characteristic, the method includes a step of illuminating the measurement volume with light at a wavelength that is selected to generate a fluorescence phenomenon, a step of measuring the fluorescence generated in the measurement volume, and a step of classifying events including a sub-step of adjusting a fluorescence separation threshold that is calculated from statistical parameters of the particles encountered, i.e. the maximum and the standard deviation.

By adding a fluorescence measurement to the RES×EXT or VOL×IDX measurements, it is possible to perform classification on the basis of three measurements giving distinct pieces of information about the events.

According to a particular characteristic, the step of classifying events identified as erythrocytes separates erythrocytes from reticulocytes as a function of a threshold based on measuring fluorescence and corresponding to the erythrocyte maturity limit, the threshold having a default value that is suitable for being adjusted in automatic manner.

Advantageously, the method includes a step of calculating the corpuscular hemoglobin concentrations of particles classified in the reticulocyte population by using an affine expression that is a function of their refringence IDX.

The invention makes it easier to calculate the corpuscular hemoglobin by using the known link between corpuscular hemoglobin and IDX, including for populations of reticulocytes.

According to a particular characteristic, the step of classifying events identified as lymphocytes or monocytes separates from the other particles having a high content of nucleic acid (in particular RNA) as a function of a threshold for fluorescence measurements that corresponds to the maturity limit of mononuclear leukocytes, the threshold having a value by default and being suitable for being adjusted in automatic manner.

According to a particular characteristic, the step of classifying events identified as neutrophilic or eosinophilic separates granulocytes and immature granulocytes as a function of a fluorescence measurement threshold that corresponds to the granulocyte maturity limit, the threshold having a value by default and being suitable for being adjusted in automatic manner.

The invention thus provides a method of classifying and flow measuring the refringence of at least two populations of particles present in a fluid. The method uses a light source of short coherence time, with a coherence length Lc<100 µm, used under extinction conditions at a center wavelength that is selected as a function of a range of volumes and a range of refractive indices expected for the particles under consideration. The method uses a device that co-operates with the light source to form a converging illuminating beam of aperture angle that is selected as a function of the range of volumes and the range of refractive indices expected for the particles under consideration at the selected center wavelength. The fluid with particles is then caused to flow through a measurement orifice in order to measure variations of impedance (RES) as the particles pass through. The fluid with particles flows through the measurement window illuminated by the beam, and extinctions EXT are measured on the axis of the beam as the particles pass through the measurement window, with this being done by means of a device or detector having a converging reception beam of aperture angle that is selected as a function of the range of volumes and the range of refractive indices expected for the particles under consideration. The method merges the RES and EXT data in order to extract therefrom events that make it possible to evaluate a relative refractive index for each event and to classify all of the events by means of at least one parameter selected from RES, EXT, or IDX.

BRIEF DESCRIPTION OF THE DRAWINGS

Other characteristics and advantages of the present invention appear from the following description made with reference to the accompanying drawings that show an implementation without any limiting character. In the Figures:

FIGS. 1A and 1B show the results obtained in an impedance/laser diffraction plane with a prior art device, respectively with a reagent having low sphering power and with a reagent having strong sphering power;

FIG. 2 is a diagram of a device of the invention;

FIGS. 3A and 3B show the results obtained in an impedance/extinction plane with a device of the invention, respectively with a reagent having a weak sphering index and with a reagent having a strong sphering index;

FIGS. 16A and 16B show the implementation of the sub-step of adjusting the resistive separation;

FIGS. 17A to 17C show the implementation of the sub-step of adjusting the extinction separation;

FIGS. 22A and 22B show a classification comparison for a case with macroplatelets;

FIG. 23 shows the classification of leukocytes on an RES× EXT matrix;

FIGS. 29A and 29B show a VOL×CHC matrix of erythrocytes in pale gray and reticulocytes in black, and a VOL×CHC matrix of reticulocytes on their own; and FIG. 30 shows how immature cells are distinguished in fluorescence for white blood cells on an EXT×FLUO matrix.

DETAILED DESCRIPTION OF AN IMPLEMENTATION

Figure 4:
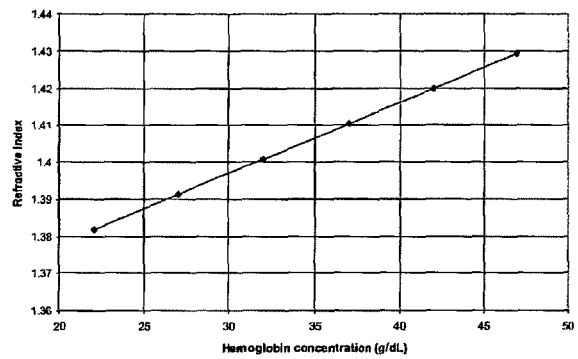
FIG. 4 shows the refractive index of an aqueous solution as a function of the corpuscular hemoglobin concentration.

In its simplest version, the method relies on measuring two parameters of a suspension of cells taken from a total blood sample diluted in a specific reagent. The reagent may be an isotonic diluant such as "ABX diluant" that is sold by the supplier Horiba Medical, or it may be a differential lysis reagent, e.g. using the "Leukodiff" reagent also sold by the supplier Horiba Medical that performs total lysis of red blood cells while preserving all of the nucleated cells coming from circulating blood. The suspension of cells is characterized by the number of cells per microliter, which itself depends on the analysis system. For example, when the suspension of cells is analyzed with the help of a flux cytometry device using the principle of hydro-focusing, the dilution of the total blood by an isotonic diluant is of the order of 1:1000. When the reagent is for differential lysis, the dilution is of the order of 1:100. These dilution levels for the total blood sample thus make it possible to prepare suspensions of cells having 10 to 10,000 cells per microliter for blood that may be normal or diseased. The two characteristics of the cells that are measured, namely 1) cell volume V by the electric method, and 2) the optical extinction signal, are then obtained using the device shown diagrammatically in FIG. 2.

The device shown in FIG. 2 comprises a light source S, a condensing lens L1, a diaphragm D1, a projection lens L2, a collecting lens L3 for collecting an image of the reticle D'1, a photoelectric detector D2, and a focusing nozzle BFC.

FIGS. 3A and 3B are obtained from the device shown in FIG. 2 operating in optical extinction conditions instead of in the laser diffraction conditions of prior art devices.

FIG. 3A was obtained with a device of the invention using the "Fluored" reagent sold by the supplier Horiba ABX (patent FR 2 759 166). FIG. 3B was obtained with the device of the invention using a reagent having a strong sphering power from the supplier Bayer. It should be observed at this point that the figures are comparable both in terms of the positions of event groups and in the shapes of the groups.

Comparing these figures with FIGS. 1A and 1B, it can be seen that the device of the invention provides better tolerance relative to the shape of the measured particles.

In the embodiment shown in FIG. 2, a capillary having a diameter of 125 μm directs the suspension of cells into a focusing nozzle BFC constituted by a small hole having a diameter of 50 μm. A secondary fluid, represented by arrows, serves to center the suspension of cells until it passes through the measurement orifice. This orifice is used for implementing volume measurement by the electric method. A constant current passes through the orifice. When a particle passes through the orifice, the impedance of the channel is modified and produces a variation in the voltage across the terminals of the counting hole. This voltage is proportional to the volume of the particle. This measurement method is known and none of the electronic arrangements needed for implementing it are described in this specification.

Thereafter, the particles are conveyed into an optical analysis window obtained by projecting a reticle of light of intensity that is as uniform as possible. Optical extinction is measured on each particle. It should be observed that according to the invention the illuminating beam is a converging beam and is characterized by its numerical aperture $NA=\sin u$, where $u$ is the half-aperture angle at the diaphragm D1.

In the measurement vessel, the numerical aperture of the illuminating beam is $NA1=n*\sin u$.

Uniform illumination is traditionally obtained by a Köhler type set-up. The principle of Köhler illumination consists in imaging the light source S in the pupil of the lens L2. This makes it possible firstly to have a single image of the source S situated in the pupil of the lens L2, and secondly to make the distribution of light in the image of the reticle D'1 uniform.

The illumination system may also be based on using a shaped optical fiber as described in patent WO 2006/053960 in the name of the Applicant.

The size of a light bench depends on the size of the optical window and also on the aperture of the beam in the counting cell. It is possible to define the Lagrange invariant $I=hu$ in the plane P1, where $h$ is the half-height of the measurement window and $u$ is the half-aperture angle of the beam. The value of this invariant is retained at all points in the optical system. Using the notation $d$ for a characteristic dimension of the diaphragm D1, and $\theta$ for the half-aperture angle at the diaphragm D1, the following relationship applies:

$$I=hu=d\theta$$

Thereafter, the light flux, written $\phi$, intercepted by the diaphragm and collected by the lens L2 is equal to the product of the geometrical extent of the beam, written G, multiplied by the luminance L of the source S, i.e. $\phi=LG$. Since in a loss-less optical system luminance L is conserved, this flux is fixed by the geometrical extent $G=\pi S \sin^2 \theta$ where S is the area of the diaphragm and $\theta$ is the half-aperture angle.

Without loss of generality, it may be assumed that the diaphragm is square and of side $d$. The flux is then given by the following expression:

$$\phi=LG=L\pi d^2 \sin^2 \theta \approx L\pi d^2 \theta^2 \text{ i.e. } \phi \approx \pi L I^2$$

It is thus shown that the flux is proportional:
- to the luminance L of the source, this parameter being a characteristic of the source and defined as being the flux emitted per unit area and per unit solid angle (watts per square meter per steradian (w/m²/sr); and
- to the square of the Lagrange invariant I, this parameter being fully determined by the geometrical data of the beam inside the counting cell.

It is important to observe that once I is set beside the measurement chamber, it is possible to vary only the luminance of the source in order to increase the power in the optical system.

In practice, the diaphragm is of rectangular shape and its dimensions are determined by two considerations. The greater dimension is determined by the size of the sheathing fluid, this diameter being substantially the diameter of the orifice used for volume measurement, having a diameter of about 60 μm. This dimension is thus set at around 100 μm.

The smaller dimension determines the spatial resolution of the measurement, which is the ability to discriminate between two cells that are very close together. Ideally, this dimension should be as small as possible. For a biological particle passing through the light window at a speed v, the smallest dimension of the window defines the duration of the exposure of the cell to the light flux and thus the duration of the electric pulse that corresponds to the physical phenomena of absorption and of diffraction. In practice, this dimension is of the order of 30 μm. It should be observed in passing that this aspect ratio for the analysis window is then about 3.

Ideally, the optical measurement should be made as close as possible to the outlet from the focusing nozzle. At this location, the particle is in a position that is well defined because of the coherence of the fluid stream. It is thus quite natural to focus the light immediately after the outlet from the focusing nozzle BFC. If the distance from the focus to the outlet of the nozzle is written x and if the radius of the nozzle is written y, then $u_{max}=x/y$. Thus, the smaller the size of the nozzle, the greater it is possible to make the aperture of the beam and the better the photometric balance.

In order to terminate this description of the optical characteristics of the device of the invention, it should be observed that setting the parameter G which is the magnification of the imaging optics, leads to the system being completely defined. This parameter is determined by space considerations.

A diaphragm of large size needs to be placed very far away from the lens L2, whereas a diaphragm of small size makes it possible to use a set-up that is more compact, since it is located closer to the lens L2. From the Lagrange invariant, it is possible to set the parameter $\theta$ in arbitrary manner. Thus, the size of the diaphragm D1 is given by the relationship $d=I/\theta$. Once this has been set, the magnification $G=h/d$ is fully determined.

If a working distance is set, as marked $\beta$ on the device of FIG. 2, then the corresponding value $\alpha=\beta/G$ is a value that is determined. It should be observed that the parameter $\beta$ is itself set by the thickness of the wall of measurement chamber, generally made of glass or quartz, and the thickness of the fluid that needs to be passed through in order to reach the stream of particles represented by dots along the axis of symmetry of the focusing nozzle BFC. This optical thickness should be taken into consideration when setting the working distance $\beta$ for reasons of available space. Finally, the focal length of the lens is also determined since $f=\alpha\beta/(\alpha+\beta)$. This sets the optical and geometrical data of the FIG. 2 set-up to a first order.

The light that is diffracted, reflected, or absorbed by a particle gives rise to a disturbance in the propagation of the light, which disturbance is detected by a receiver constituted by the lens L3 and by the detector D2. All of the signals contribute to measuring optical extinction referred to below as extinction and written EXT.

The association of the lens L3 with the detector D2 constitutes the receiver portion of the set-up. In the simplest version of the set-up, the numerical aperture of the reception light beam is equal to that of the illuminating beam.

The numerical aperture NA2=n*sin(v) is the numerical aperture of the receiver optics.

In the simplest version of the set-up, the numerical aperture of the reception light beam is equal to that of the illuminating beam. Thus NA2=NA1. Since the microparticle is illuminated and measured in the same fluid of refractive index n, it can thus be deduced that the angles u and v are equal.

More generally, the illuminating beam need not have the same numerical aperture as the beam used for observing the microparticle. This is well known in optical microscopy where the numerical aperture defines the level of coherence of the illuminating beam. Furthermore, since diffraction phenomena are generally functions of the coherence of the fields at the illuminated object, it is to be expected that the response of the optical system depends on the numerical aperture NA1 of the illuminating system.

It is known that the coherence radius of the light field in the plane through which the microparticle passes is of the order of rc=$\lambda$/w where $\lambda$ is the center wavelength and w is the apparent diameter of the illuminating pupil. This is a consequence of the theorem of Van Cittert-Zernike. By way of example, reference may be made on this topic to the work by L. Mandel and E. Wolf "Optical coherence and quantum optics", Cambridge University Press, 1995, p. 188.

Thus, in the invention, it may be necessary to modify the spatial coherence of the illumination at the measurement point depending on the more or less sensitive extent to which the optical extinction needs to incorporate morphological information for which the extent of spatial frequencies may be greater or smaller. For example, if a particle has high spatial frequencies, as a result of surface granularity or indeed of granules internal to the particle, as can happen with certain leukocytes or platelets, it is possible to reduce the coherence of the illumination by reducing the numerical aperture of the condenser lens. Under such circumstances, the illuminating beam does not have sufficient spatial resolution to reveal the presence of these high spatial frequencies and the measurement of optical extinction would be sensitive to such granularity. Otherwise, interaction with granules is to be enhanced and the optical extinction measurement is to be correspondingly more marked. In other words, in application of Abbe's theory on the formation of images, the spatial frequencies of the particle under analysis diffracts the incident light.

This interaction gives rise to a spectrum that is characterized by the angular dispersion of the light after it has interacted with the analyzed object. The objective lens used for observation constitutes a spatial filter that passes only some of the spatial frequencies. The passband of the filter is defined by the numerical aperture NA2. For a more detailed description of the angular spectrum and of the effects of coherence, reference may be made to the work by Joseph W. Goodman entitled "Introduction to Fourier optics" (3rd edition, Roberts & Company, Anglewood, Colo., 2005, p. 127, Chapter 6). The work of S. Slansky of the Paris "Institut d'Optique" provides information about the simultaneous roles of NA1 and NA2 for objects that are very simple such as a black dot on a white background, and shows that contrast is optimized by an appropriate selection of the ratio NA1/NA2.

Reference may also be made for example to the article by S. Slansky "Influence de la cohérence de l'éclairage sur le contraste de l'image d'un point noir en présence d'un petit défaut de mise au point" [The influence of the coherence of illumination on the contrast in the image of a black dot in the presence of a small focusing error] (Journal of Modern Optics, Vol. 2, No. 3, October 1955).

Although the invention does not make use of the concept of contrast, such concepts can be likened to the effective refringence measurements of the invention that include structural information at spatial frequencies that may be greater or smaller. Finally, the effective refringence of the particle under analysis corresponds to the refringence of a uniform sphere of volume V identical to the volume of the particle under analysis, and producing the same optical extinction phenomenon as the particle itself on the same device characterized by (NA1, NA2, Lc, $\lambda$, a, b) where NA1 is the numerical aperture of the illumination, NA2 is the numerical aperture of reception, Lc is the coherence length of the source, $\lambda$ is the center wavelength, a is the short dimension of the analysis optical window which is in the travel direction of the particle, and b is the long dimension of the analysis optical window, which is perpendicular to the travel direction of the particle. A numerical analysis of the concept of effective refractive index is set out for example by A. Doicu and T. Wriedt in their article entitled "Equivalent refractive index of a sphere with multiple spherical inclusions" (J. Opt. A: Pure Appl. Opt. 3 (2001), pp. 204-209).

Finally, it should be observed that it is possible to use pupils of some other type, e.g. annular pupils. Such solutions correspond to special cases of the invention that are not described in detail. Finally, it should be observed that the choice of parameters for the system, NA1, NA2, Lc, $\lambda$, a, and b, depends to a large extent on the characteristics of the particles for analysis.

Below, the values selected for these parameters are illustrated for measuring refractive indices of circulating blood cells. The following characteristics are used:

NA1=NA2=0.3, Lc=15 µm, $\lambda$=0.650 µm, a=30 µm, b=90 µm

The particle that passes through the light window absorbs and disperses the light of the illuminating beam. These two phenomena contribute to reducing the DC component of the photoelectric signal that is referred to herein as "extinction".

The invention is linked with interpreting the mechanisms of wave/particle interaction. This interaction is the subtle result of the interference of the incident wave and of the wave diffused by the particle under analysis, as described below.

Use is made of the theoretical approach of Van de Hulst, an approximate theory of the diffraction phenomenon, and also known as the anomalous diffraction theory.

Studying the interaction of a plane wave with a uniform sphere is of use insofar as, according to the invention, a biological particle interacts with the light beam at the vicinity of the focal plane. In this plane, the wave structure is substantially plane. This wave, as represented by the complex electric field may be written as follows:

$$E_o = e^{-ikz+\omega t}$$

Assuming that the amplitude of this wave is unity, the diffused wave is then modeled by a spherical wave having the following form:

$$E_{sca} = S(\theta) \frac{e^{-ikr+\omega t}}{ikr}$$

This expression involves a function $S(\theta)$ that represents the amplitude of the wave diffused by the biological particle. In particular, it reveals information about the spatial distribution of the diffused wave as a function of the parameter $\theta$.

By definition, the extinction parameter is defined for $\theta$=0, and it is written Cext.

Below, it is shown that this extinction parameter Cext may be expressed as a function of the function $S(\theta)$.

Close to the optical axis of the device, the following approximation can be observed:

$$r = (x^2 + y^2 + z^2)^{1/2} = z\left(1 + \frac{x^2+y^2}{z^2}\right)^{1/2} \approx z\left(1 + \frac{x^2+y^2}{2z^2}\right)$$

Providing x,y<<z, the wave in the vicinity of the axis z may be written:

$$E_{sac} + E_0 = S(\theta = 0)\frac{e^{-ikz\left(1+\frac{x^2+y^2}{2z^2}\right)+\omega t}}{ikz} + E_0$$

$$= S(\theta = 0)\frac{e^{-ikz+\omega t}e^{-ikz\left(\frac{x^2+y^2}{2z^2}\right)}}{ikz} + E_0$$

$$= S(\theta = 0)\frac{E_0 e^{-ikz\left(\frac{x^2+y^2}{2z^2}\right)}}{ikz} + E_0$$

$$= E_0\left\{S(\theta = 0)\frac{e^{-ikz\left(\frac{x^2+y^2}{2z^2}\right)}}{ikz} + 1\right\}$$

The intensity is obtained by taking the square of the modulus of this complex number:

$$I(x, y) = |E_{sca} + E_o|^2 = |E_0|^2\left\{1 + \frac{2}{kz}\text{Re}\left\{\frac{S(\theta = 0)}{i}e^{-ikz\left(\frac{x^2+y^2}{2z^2}\right)}\right\}\right\}$$

The term in braces is then the modulus of a complex number 1+w. Furthermore, the second-order term is negligible compared with 1 since it is assumed that z is sufficiently large.

This intensity may be integrated in the area of a small pupil centered on the axis z. This integral is written as follows:

$$\iint_{pupil} I(x, y)dxdy =$$

$$Io\iint_{pupil} dxdy + \frac{2Io}{kz}\iint_{pupil}\text{Re}\left\{\frac{S(\theta = 0)}{i}e^{-ikz\left(\frac{x^2+y^2}{2z^2}\right)}\right\}dxdy$$

This integral indicates that the flux of photons passing through the pupil is the resultant of two terms: the first term represents the photon flux in the absence of the biological particle, and the second term represents the photon flux in the presence of the particle, which particle extracts a fraction of the pupil by diffraction. Light flux conservation requires this term to be negative.

Using the notation of H. C. Van de Hulst, the following can be written:

$$\iint_{pupil} I(x, y)dxdy = O - C$$

Still using Van de Hulst notation, the second term is made up of two Fresnel integrals each involving the term $(2\pi z/ik)^{1/2}$. In the limit where integration is extended to $\infty$ in the (x,y) plane, the following fundamental formula can be deduced:

$$C_{ext} = \frac{4\pi}{k^2}\text{Re}\{S(\theta = 0)\}$$

where $k=2\pi/\lambda$
and $$Q_{ext} = \frac{4}{x^2}\text{Re}\{S(\theta = 0)\}$$

where x=ka, with a being the radius of the particle.

It is thus possible to determine the function $S(\theta=0)$ by simple geometrical considerations.

The reasoning of Van de Hulst makes it possible to determine this function by calculating the following $$S(\theta = 0) = \frac{k^2}{2\pi}\iint[1 - e^{-i\rho\sin\varphi}]dxdy$$

where the integral is taken in the shadow projected by the biological particle.

This integral may be calculated exactly in order to give the following expression:

$$S(\theta=0^\circ)=x^2K(i\rho)$$

where:

$$K(w) = \frac{1}{2} + \frac{e^{-w}}{w} + \frac{e^{-w}-1}{w^2}$$

Thus, by averaging these results, it is possible to write the extinction coefficient in the following form:

$$Q\text{ext}=2-(4/\rho)\sin\rho+(4/\rho^2)(1-\cos\rho)$$

$$\rho=2(2\pi/\lambda)a|m-1|$$

m=IDX corresponding to the refringence of the microparticle as defined in the introduction to this specification. For a red blood cell, m may be given by the following formula:

$$m-1=(\alpha/no)*Hc-i(\text{Ln }10/\pi M)*(\lambda\in_{\mu m}/no)Hc$$

It should be observed that the refringence of the red blood cell, and in general manner of any particle, is represented by a complex number. The real part has an influence on the phase of the incident wave. By way of example, it may be the result of the analysis and observations performed by R. Barer and S. Joseph in the article entitled "Refractometry of living cells" (Quarterly Journal of Microscopical Science, Vol. 95, Part 4, pp. 399-423, December 1954). The imaginary part is responsible for the absorption and its development results in no more than the application of the Beer-Lambert law.

The signal Si from the detector D2 may be calculated using the following formula:

$$Si=Po-Q\text{ext}*Po*(\pi r^2/a\times b)$$

After the photoelectric signal has been filtered by a high-pass type electronic circuit, the extinction generated by the presence of the particle is determined using the following formula:

$$EXT=Po*Q\text{ext}*(\pi r^2/a\times b)$$

With the following numerical data:

no=1.34, the refractive index of the cytoplasm in the absence of hemoglobin taken as being equal to the refractive index of the fluid in which the red blood cell is immersed;

$N_L$=1.335, the refractive index of the fluid in which the particle is immersed;

α=0.0019 deciliters per gram (dL/g), a constant that depends on the solute, here hemoglobin;

Hc=22 g/dL to 46 g/dL, the range over which corpuscular hemoglobin varies;

M: 66650 daltons (D), the molecular mass of hemoglobin;

λ=0.650 μm, the illuminating wavelength;

∈ μm: 0.2520 square centimeters per micromole ($cm^2$/μmol), the molar extinction coefficient;

Po=1.00 microwatts (μW), the power of the light beam;

a=33 μm, the short dimension of the analysis window; and b=100 μm, the long dimension of the analysis window.

Taken together, this theoretical and numerical data makes it possible to predict the curve of FIG. 4 which shows the refractive index IDX of a red blood cell as a function of hemoglobin concentration.

Figure 5:
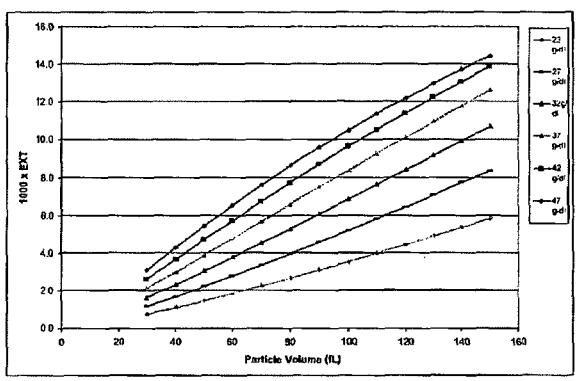
FIG. 5 shows the apparent extinction value of a red blood cell as a function of its volume and of the corpuscular hemoglobin concentration (g/dL) for $\lambda=650$ nm and NA=0.3.

FIG. 5 shows more precisely the extinction signal EXT as a function of the volume V of a spherical particle for various equivalent values of hemoglobin concentration. FIG. 5 shows that for a given volume, the more hemoglobin there is in a red blood cell, the greater its extinction.

This set of curves is the result of the above-described calculation seeking to show that the extinction signal of a red blood cell is a function not only of its volume, but also of its refringence, which is itself linearly dependent on its hemoglobin concentration.

Figure 6:
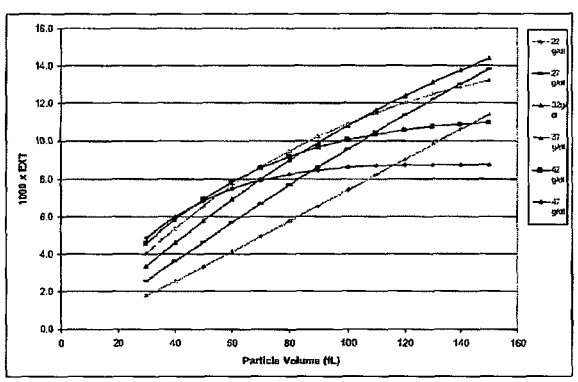
FIG. 6 shows the apparent distinction value of a red blood cell as a function of its volume and of the corpuscular hemoglobin concentration (g/dL) for $\lambda=405$ nm and NA=0.3.

This solution is not trivial since at the wavelength of 405 nm, the set of curves that are calculated is as shown in FIG. 6, indicating that there is no unique solution for determining (CHC, V), which means that these parameters cannot be measured at that wavelength.

Figures 7, 8:
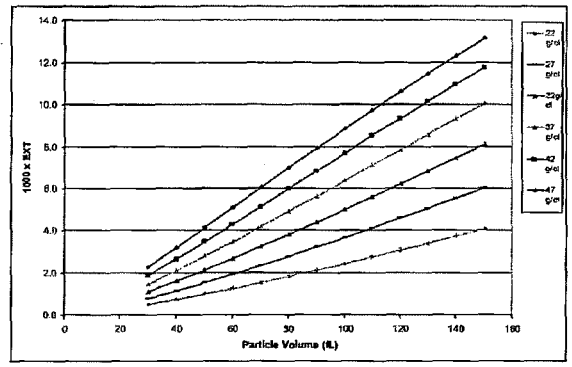
FIG. 7 shows the apparent distinction value of a red blood cell as a function of its volume and of the corpuscular hemoglobin concentration (g/dL) for $\lambda=800$ nm and NA=0.3.
FIG. 8 compares the results of measuring the mean corpuscular hemoglobin concentration (MCHC) of 28 blood samples covering high and low values of this parameter for two distinct analyzers.
Figure 9A:
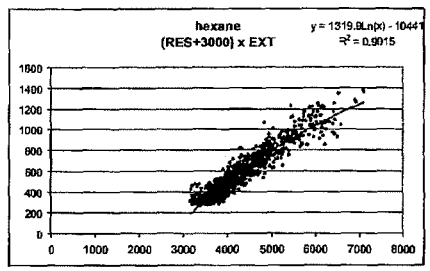
FIGS. 9A to 9F show measurements of emulsions using the device of the invention, respectively with hexane, heptane, octane, nonane, decane, and dodecane.
Figure 9B:
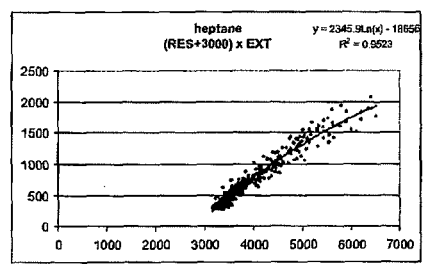
Figure 9C:
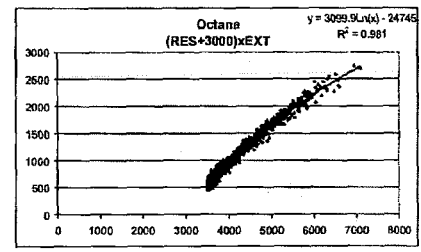
Figure 9D:
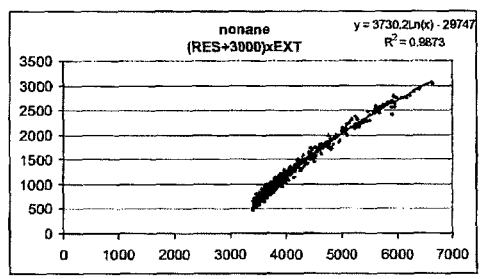
Figure 9E:
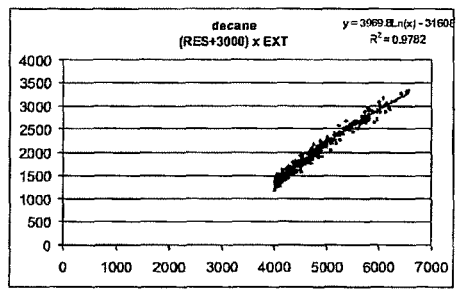
Figure 9F:
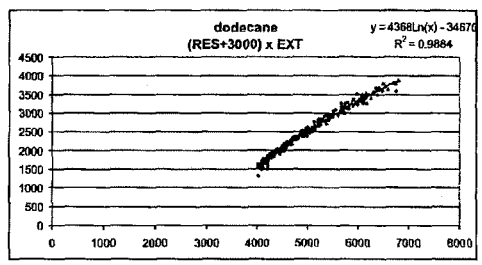

In contrast, measurement in the infrared is more favorable, as shown in FIG. 7, where the illumination wavelength is 800 nm.

FIG. 8 compares the results of measuring the mean corpuscular hemoglobin concentration (MCHC) parameter for 28 blood samples covering both high and low values for this parameter. The abscissa axis corresponds to the MCHC value obtained by an analyzer of the Horiba ABX range (Pentra 120), whereas the ordinate axis gives the value of this parameter as determined by the method of the invention and corresponding to the mean calculated over all of the erythrocytes for which the CHC parameter was measured. It should be observed that the result ($R^2$≈0.9) is satisfactory given, firstly, the small amplitude of this parameter which is a Wintrobe constant, and secondly, the difference in the methodologies applied for determining this parameter. On a hematology analyzer, a plurality of independent measurements are combined to determine the value of MCHC, for example: the total number of red blood cells written #RBC, the mean cell volume written MCV, and the weight of hemoglobin in the sample written Hb, using the following formula:

MCHC calculated=$Hb/(HT$=MCV×#RBC)

In the invention, the MCHC is derived directly from the impedance and extinction measurements, such that the calculation involves only two independent measurements instead of three.

In practice, the device used for acquiring the experimental data is the device shown in FIG. 2. Prior to taking the measurements of the method of the invention, a blood sample is diluted with a reagent selected for making red blood cells spherical. The sphering power is typically obtained by a surfactant. The reagent may also include a dye or a fluorochrome. The presence of these chemical elements makes it possible to measure other properties of cells, e.g. such as described in patent FR 2 759 166 in the name of the Applicant.

Given that this measurement principle is known, the description below relates to the model for inversion, i.e. for determining the parameters of the spherical particle as a function of the extinction measurements and the measurements of volume by the impedance method. The purpose is to make it possible to invert the measurements that are taken.

The inversion model is advantageously determined on the basis of experimental data so as to avoid being affected by the approximations and assumptions included in solving the forward problem.

In order to solve the inversion problem, a set of emulsions was prepared from organic solvents selected to have refringences that are known and close to those of the biological particles for analysis.

For red blood cells, the solvents selected were of the alkane family for which the refractive indices lie in the range of interest at the illumination wavelength of 650 nm.

The following table thus gives the values of the refractive indices IDX of the solvents used:

| | |
|---|---|
| heptane | 1.39 |
| octane | 1.4 |
| nonane | 1.405 |
| decane | 1.41 |
| dodecane | 1.42 |

Observing the emulsions made it possible for each series (hexane, heptane, . . . ) and thus for each refractive index, to model the optical extinction response as a function of the volume as measured by impedance.

Various models could be used. Below, the model selected for solving the problem is a logarithmic model. the extinction response EXT of a series i is then modeled by:

$$EXT = k_i \cdot \ln(RES+t) + o_i$$

where $k_i$ and $o_i$ are parameters of the series and t is a constant, in this example 3000 for the RBC/PLT channel, serving to improve the fit of the models $k_i$ and $o_i$. It should be observed here that the constant t varies as a function of the machine used and as a function of the particles being analyzed. In particular, it may be different when analyzing white blood cells.

Experience shows that such logarithmic models that can be used for establishing the correspondence between the (volume×extinction) responses of an emulsion. An emulsion of each solvent produces a set of droplets having volumes that are distributed continuously over the measurement range of the device of the invention. Each droplet has a refractive index that is well defined by the nature of the solvent.

This is shown by FIGS. 9A to 9F where each droplet is represented by a point on the plane defined by an abscissa axis value corresponding to the volume V of the droplets (the scale being shown here in terms of number of channels), and by an ordinate axis value corresponding to the extinction of the droplet, also expressed in terms of number of channels.

A calculated interpolation function for each measurement is marked on the graph in the form $$y = k_i \cdot \ln(x+t) + o_i$$

where i is the index of the solvent.

The inverse problem thus consists for an unknown refractive index in determining the parameters of the logarithmic model, i.e. the parameters $k_i$ and $o_i$.

The experimental data obtained produces the following targets for the range of indices under consideration:

|      | idx   | k    | o      |
|------|-------|------|--------|
| hex  | 1.38  | 1320 | −10441 |
| hept | 1.39  | 2346 | −18656 |
| oct  | 1.4   | 3100 | −24745 |
| non  | 1.405 | 3730 | −29747 |
| dec  | 1.41  | 3970 | −31608 |
| dodec| 1.42  | 4368 | −34670 |

Figure 10:
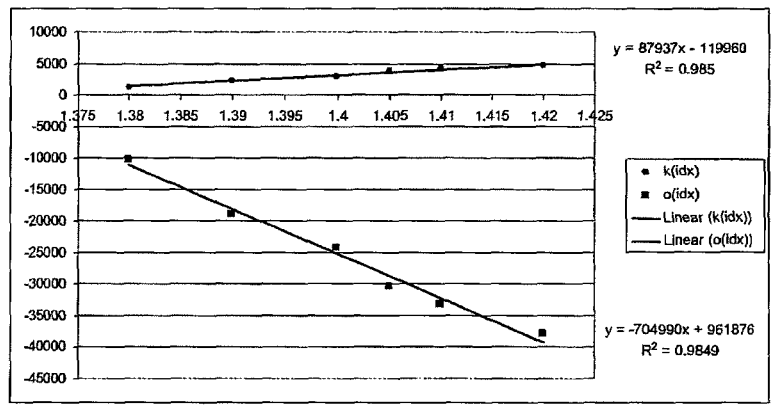
FIG. 10 shows modeling of the parameters k and o as a function of refractive index.

It is thus possible to model these coefficients coarsely as a function of index by the affine approximations shown in FIG. 10.

The following equations are thus obtained where i is the index:

$$k_i = a \cdot i + b$$

$$o_i = c \cdot i + d$$

where a, b, c, and d were obtained by said affine approximation. In FIG. 10, the parameters are:
a=78519, b=−106853, c=−624927 and d=850440

Associating this linear approximation of the coefficients with the logarithmic model makes it possible to solve the inverse problem on the basis of experimental coefficients.

$$EXT = k_i \cdot \ln(RES + t) + o_i$$
$$= (a \cdot i + b) \cdot \ln(RES + t) + c \cdot i + d$$
$$= (a \cdot \ln(RES + t) + c) \cdot i + b \cdot \ln(RES + t) + d$$

whence:

$$i = (EXT - b \cdot \ln(RES+t) - d)/(a \cdot \ln(RES+t) + c)$$

The extinction level for a given volume measured by impedance thus makes it possible to determine the refractive index.

Figure 11:
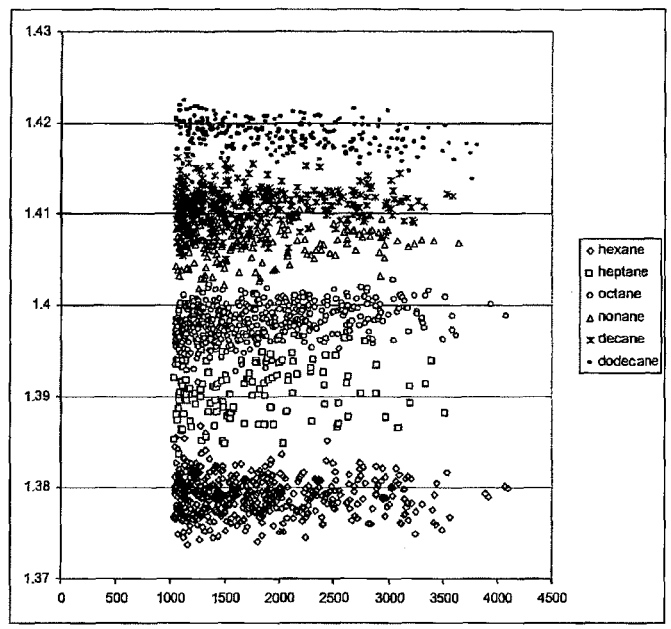
FIG. 11 shows the representation of various emulsions in a plane having RES as its abscissa axis and calculated refractive index as its ordinate axis.

This ability to determine the index is shown by determining the indices of the emulsions used in the experiment. This result is shown in FIG. 11.

Below, there follows a description of the method of separating erythrocytes and thrombocytes using the method of the invention.

The principle of this separation of erythrocytes, written RBC, and the platelets, written PLT, relies on two discriminating criteria. The first is used by most manufacturers of automatic hematology analyzers. It is volume.

With blood that is normal, the mean volume of the platelets PLT lies in the range 6 fL to 10 fL, while the red blood cells have a mean value lying in the range 80 fL to 100 fL. The measured magnitude of a resistive pulse is representative of volume, thus making it possible to classify these two populations.

A second criterion may be used to improve RBC/PLT discrimination. This is hemoglobin concentration. Platelets PLT do not have any, whereas red blood cells have a mean hemoglobin concentration lying in the range 31 g/dL to 35 g/dL. The measured magnitude of the extinction pulse which characterizes the optical masking is representative of this hemoglobin content.

It therefore appears appropriate to perform separation on the basis of the positions of events in the RBC/PLT matrix by using 2D thresholding so as to subdivide the matrix into contiguous polygons.

Figure 12:
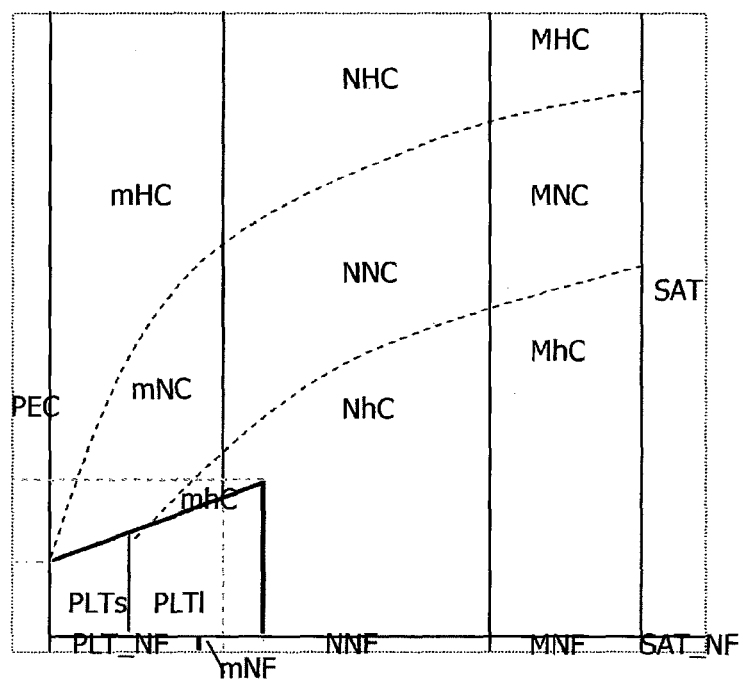
FIG. 12 shows an RBC/PLT matrix in the VOL×EXT plane.

A distinction is then added among RBC classes depending on the corpuscular hemoglobin of each cell by using a threshold that is drawn in dashed lines in FIG. 12.

The arrangement of the populations giving the shape of the RBC/PLT matrix in the RES×EXT plane is shown in FIG. 12.

The classification algorithm takes place in two stages:
classifying erythrocytes and platelets; and
sub-classifying erythrocytes depending on their hemoglobin, and platelets depending on their density.

These classifications rely on the same principle, which consists in performing gating or windowing or by performing a manual selection by selecting thresholds using an RES× EXT, a VOL×CHC (corpuscular hemoglobin concentration), or a VOL×DENS (platelet density) matrix.

A gating operation is explained below.

Firstly, a polygon is created in a frame of reference in the form of a finite number of segments, the first of which is attached to the last in order to form a polygon.

A reference point is then selected outside the frame of reference.

A test is performed to determine whether a given point lies within the polygon by counting how many segments of the polygon are crossed by the segments connecting the reference point to the point under test.

If and only if this number is odd, then the point lies in the polygon.

If the segment from the reference point to the point under test passes through a vertex to the polygon, then the reference point is moved.

Thereafter, it is tested whether two segments [P1-P2] and [P3-P4] cross as follows.

The following magnitudes are calculated initially:

$$Xa = X2 - X1$$

$$Ya = Y2 - Y1$$

$$Xb = X3 - X1$$

$$Yb = Y3 - Y1$$

$$Xc = X3 - X4$$

$$Yc = Y3 - Y4$$

$$d = Xa \cdot Yc - Ya \cdot Xc;$$

if d=0, then the segments are in alignment.

Under such circumstances, if they belong to the same straight line (slope, offset) and if, on that line, one end of a segment is situated between the two ends of the other segment, then and only then do the segments cross.

Otherwise the following is calculated:

```
{
    s = (Xa.Yb - Ya.Xb)/d
    t = (Xb.Yc - Yb.Xc)/d
    if and only if ((s<=1) and (t<=1) and (s>=0) and
    (t>=0)), then the segments cross
}
```

On the synthetic matrix shown in FIG. 12, several types of threshold are represented by drawing different types of line. The thresholds in fine lines are fixed thresholds. They are determined by parameters set by default on executing the calculation algorithm. The bold line thresholds correspond to automatic thresholds, those that can be found by the classification algorithm.

The table below gives the classes of the RBC/PLT classification algorithm.

| Class | Sub-class | Meaning |
|---|---|---|
|  | PEC | Small cellular element |
| PLT | PLTs | Small platelets |
|  | PLTl | Large platelets |
|  | PLTs_NF | Small platelets (no extinction) |
|  | PLTs_NF | Small platelets (no extinction) |
| RBC | mhC | Hypochromic microcytes |
|  | mNC | Normochromic microcytes |
|  | mHC | Hyperchromic microcytes |
|  | mNF | No-extinction microcytes |
|  | NhC | hypochromic normal erythrocytes |
|  | NNC | normochromic normal erythrocytes |
|  | NHC | hyperchromic normal erythrocytes |
|  | MNF | no-extinction normal erythrocytes |
|  | MhC | Hypochromic macrocytes |
|  | MNC | Normochromic macrocytes |
|  | MHC | Hyperchromic macrocytes |
|  | MNF | No-extinction macrocytes |
| SAT | SAT | Resistive saturation events |
|  | SAT_NF | Resistive saturation events (no extinction) |

Figure 13:
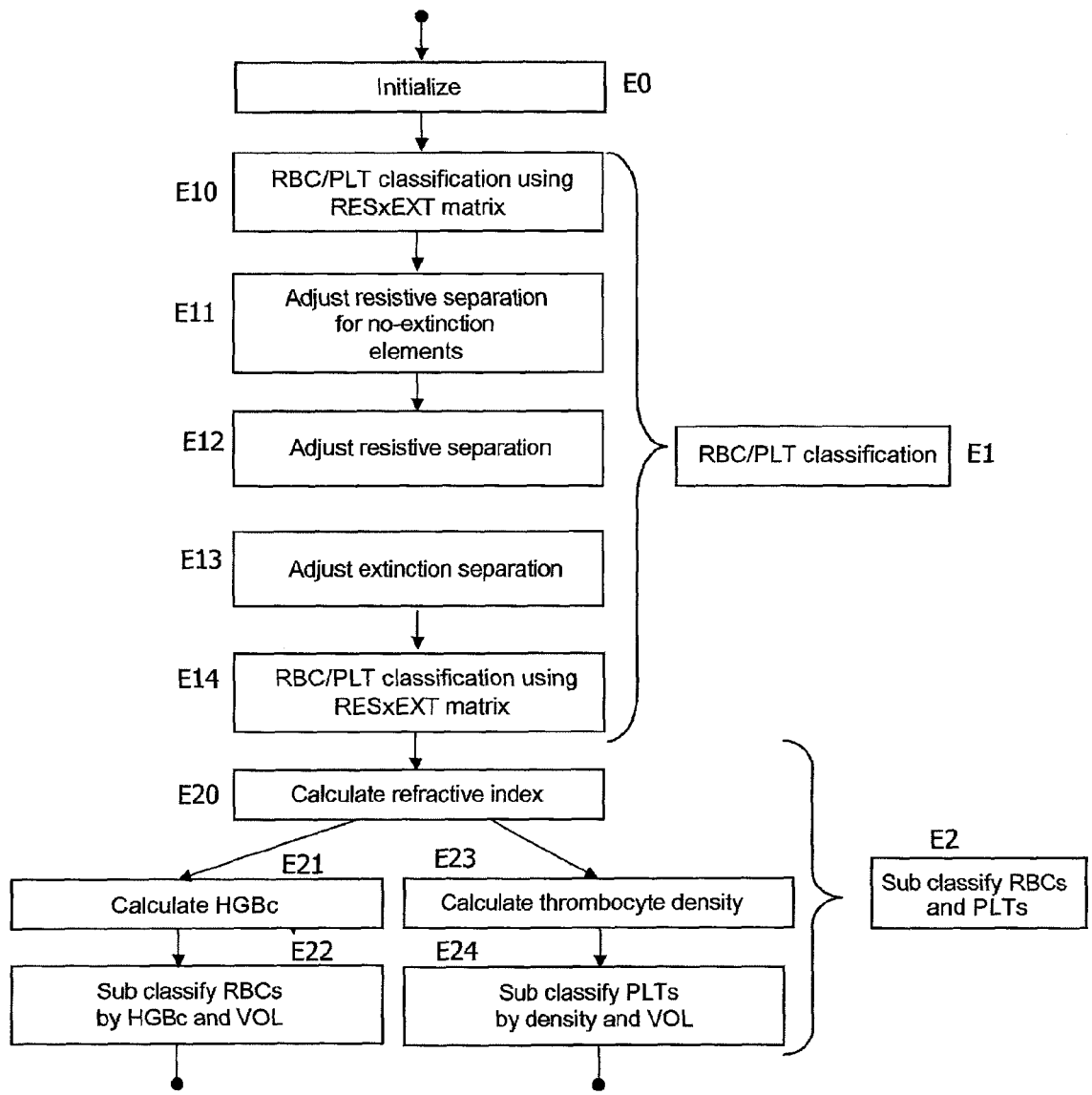
FIG. 13 is a flow chart for RBC and PLT classification.

FIG. 13 is a flow chart for the classification algorithm.

The first classification step E0 consists in initializing each event to a class NI.

Figure 14:
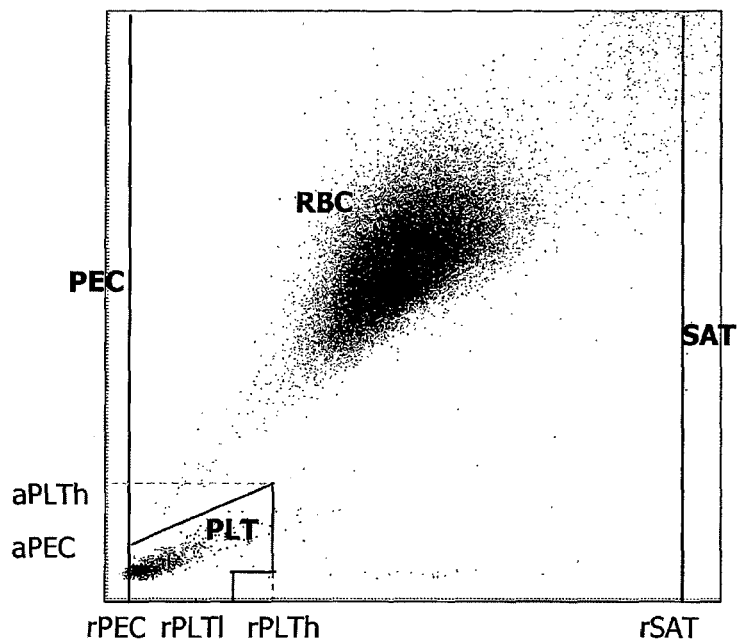
FIG. 14 shows RBC/PLT classification using the RES× EXT matrix.

This step E1 classifies all events using the RES×EXT matrix shown in FIG. 14. There then begins a step E10 of RBC/PLT classification proper.

The following populations: RBC (erythrocytes), PLT (platelets), PEC (small cellular elements), and SAT (saturated elements) are thus identified in a preliminary sub-step E10 of the RBC/PLT classification step.

Figure 15:
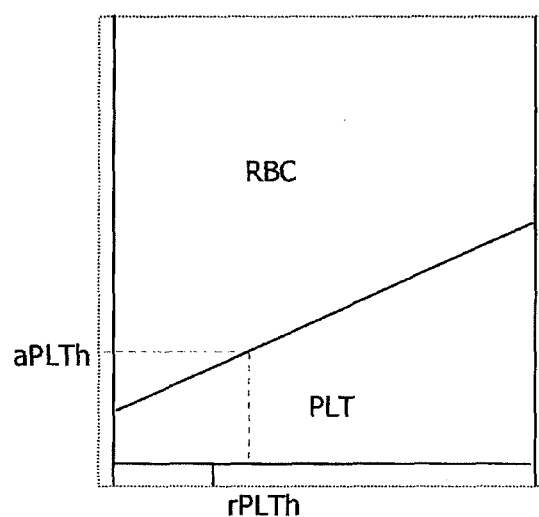
FIG. 15 shows the thresholds of the RBC/PLT matrix used during the first gating of FIG. 14.

For this first sub-step E10 that consists in a first gating operation, the thresholds rPLTh and aPLTh are used in order to have a slope and an offset at the origin for extinction separation. The separation of platelets is not restricted to rPLTh. This gating operation thus relies on the matrix of FIG. 15.

Thereafter, in a sub-step E11, an adjustment is performed of the resistive separation of no-extinction elements. This is in order to obtain good separation between no-extinction erythrocytes and platelets. Platelets that are not seen optically are of small size. This therefore justifies making no use of the volume information in order to distinguish them from erythrocytes. This option appears to be better than that which would consist in extrapolating from a threshold found using platelets with non-zero extinction.

For this sub-step E11, only events classified as platelets and erythrocytes are taken into account. Their abscissa values H_RES are evaluated in order to create a histogram. A search is made for a valley in the histogram. If the valley shows a double population of erythrocytes since the number of occurrences in the valley is large, then a search is made for another valley. Once the valley between platelets and erythrocytes has been found, if it is sufficient well-marked, then the threshold rPLTl is readjusted on the valley.

Thereafter, in a sub-step E12, an adjustment of the resistive separation is performed. For this purpose, the slope and the offset at the origin of the separation in extinction is calculated beforehand using the following expressions:

$$\text{slope} = \frac{aPLTh - aPEC}{rPLTh - rPEC}$$

$$\text{offset} = aPEC - \text{slope} \cdot rPEC$$

This is necessary when recalculating the threshold aPLTh after adjusting the threshold rPLTh in sub-step E11.

Only events classified as platelets are considered as this point. Their abscissa values H_RES are used for creating a histogram. A search is made for a valley therein. If the valley is sufficiently well-marked, the threshold rPLTl is readjusted thereon. This sub-step allows for the situation in which the extinction separation cuts through the cloud of erythrocytes.

If no valley is found or if the valley is not sufficiently distinct, then the value of rPLTh is calculated statistically. This means a priori that the extinction separation has isolated only platelets. A mean p and a standard deviation a are deduced from this cloud. This is shown in FIGS. 16A and 16B.

It is then possible to write:

$$rPLTh = \mu + rFACTOR \cdot \sigma$$

from which it is possible to deduce:

$$aPLTh = \text{slope} \cdot rPLTh + \text{offset}$$

In a sub-step E13 of adjusting the extinction separation, account is taken only of events classified as platelets and erythrocytes for which the extinction is not zero.

Thus, as shown in FIGS. 17A to 17C, a rotation is performed about the center (2048, 2048) through an angle $$\theta = 270 - a\tan(\text{slope}) \times \frac{360}{2\pi} \text{ with}$$

$$\text{slope} = \frac{aPLTh - aPEC}{rPLTh - rPEC}$$

giving new axes:

$$X_1 = \cos\theta(X - 2048) + \sin\theta(Y - 2048) + 2048$$

$$Y_1 = -\sin\theta(X - 2048) + \cos\theta(Y - 2048) + 2048$$

The abscissa values $X_1$ of the events are evaluated in order to create a histogram. A search is made for a valley therein. If the valley is sufficiently marked, the thresholds aPEC and aPLTl are then recalculated as a function thereof, otherwise they are left unchanged.

A sub-step E14 then performs RBC/PLT classification on the RES×EXT matrix with the readjusted thresholds.

A step E2 of sub-classifying RBC and PLT then takes place.

This step E2 consists in classifying sub-populations of erythrocytes and of thrombocytes.

In a first step E20, the refractive index of each particle is calculated as follows:

$$IDX = \frac{H\_ABS - b \cdot \ln(H\_RES + 3000) - d}{a \cdot \ln(H\_RES + 3000) + c}$$

with A, B, C, D, and T being coefficients that depend on experimental conditions and on the measurement cycle.

Thereafter, in order to be able to separate the hypochromic, hyperchromic, and normochromic populations of erythrocytes, it is necessary to calculate their corpuscular hemoglobin concentration (CHC) in a sub-step E21. Thus, the transformation of the refractive index into corpuscular hemoglobin concentration is applied to the erythrocytes, on the basis of the classification of the events and using the following expression:

$$HGBc = hgbcSlope * IDX + hgbcOffset$$

Figure 18:
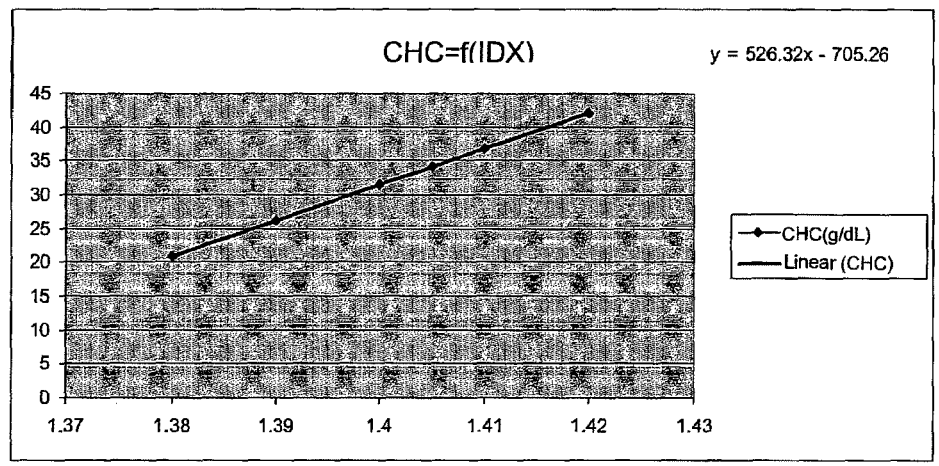
FIG. 18 shows how hemoglobin concentration is calculated from the refractive index.

FIG. 18 thus shows how corpuscular hemoglobin concentration is calculated from the refractive index.

Figure 19:
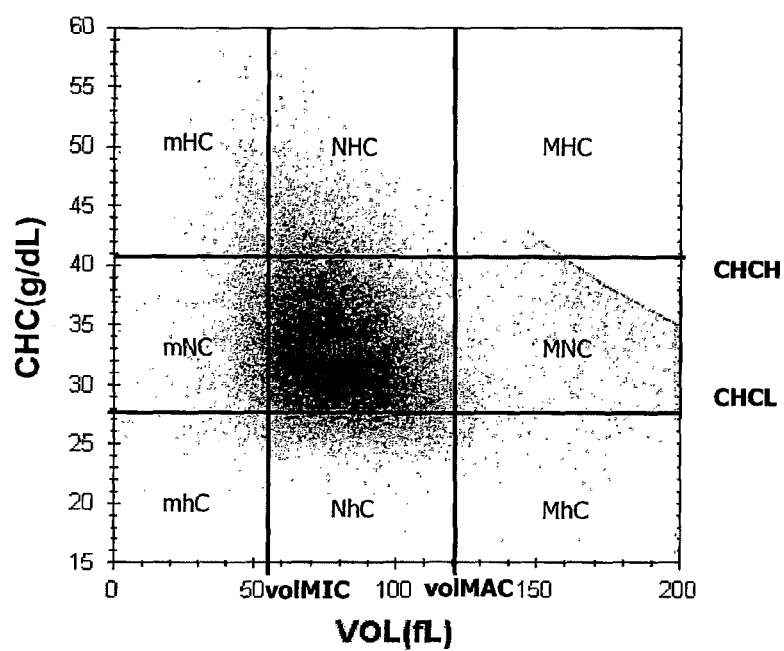
FIG. 19 shows an erythrocyte sub-classification by volume and by hemoglobin concentration.

In a sub-step E22, the erythrocytes are sub-classified by volume and by corpuscular hemoglobin concentration on the basis of the VOL×CHC matrix. This makes it possible to distinguish between hypochromic, hyperchromic, and normochromic populations and between populations of microcytes and of macrocytes. Nine sub-populations of erythrocytes are thus obtained and may be shown as in FIG. 19.

If their volume is below the threshold volMic they are microcytes, if it is greater than volMac they are macrocytes, otherwise they are considered as being normal.

Thereafter, if their hemoglobin concentration is less than the threshold CHCL, they are hypochromic, if their hemoglobin concentration is greater than the threshold CHCH, they are hyperchromic, and otherwise they are considered as being normal.

Furthermore, since platelet density provides information about platelet activation, the density of thrombocytes is also calculated in parallel in a sub-step E23. In the same manner, the thrombocyte density can thus be evaluated by another affine transformation for events classified as such, and since their volume is known from the impedance measurement, it is possible to determine dry weight:

$$PLT\_COMPO = DENS = compoSlope * IDX + compoOffset$$

Thereafter, in a sub-step E24 the thrombocytes are sub-classified by their volume and by their density.

Figure 20:
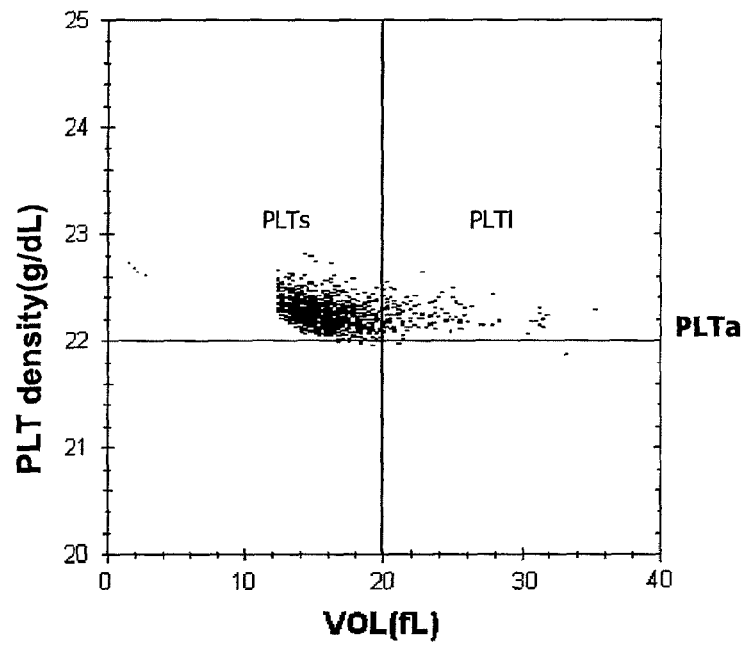
FIG. 20 shows a platelet sub-classification by volume and by density.

From the VOL×DENS matrix shown in FIG. 20, the platelets are sub-classified in order to distinguish between activated platelets, small platelets, and macroplatelets. This produces four sub-populations of platelets as can be seen in FIG. 20.

If their volume is less than 20 fL, then they are small platelets, and if it is greater than 20 fL, they are macroplatelets.

Thereafter, if their density is less than the threshold PLTa they are activated platelets.

The separation that the invention makes possible in the RES×EXT matrix is found to be very effective with microcytosis. Since the volume of the red blood cells is smaller, it tends to approach the volume of the largest platelets. It is therefore difficult in certain manner to establish separation between the largest platelets and the smallest microcytes while performing a resistive measurement only. It can thus be seen that the separation of the invention provides an advantage compared with separation that is purely resistive.

Furthermore, it is also difficult to separate platelets from microcytes solely on the basis of distinction, since the hemoglobin content of microcytes is naturally small because of their size. However, by combining these two measurements, it becomes entirely possible to achieve proper separation.

Figures 21A, 21B:
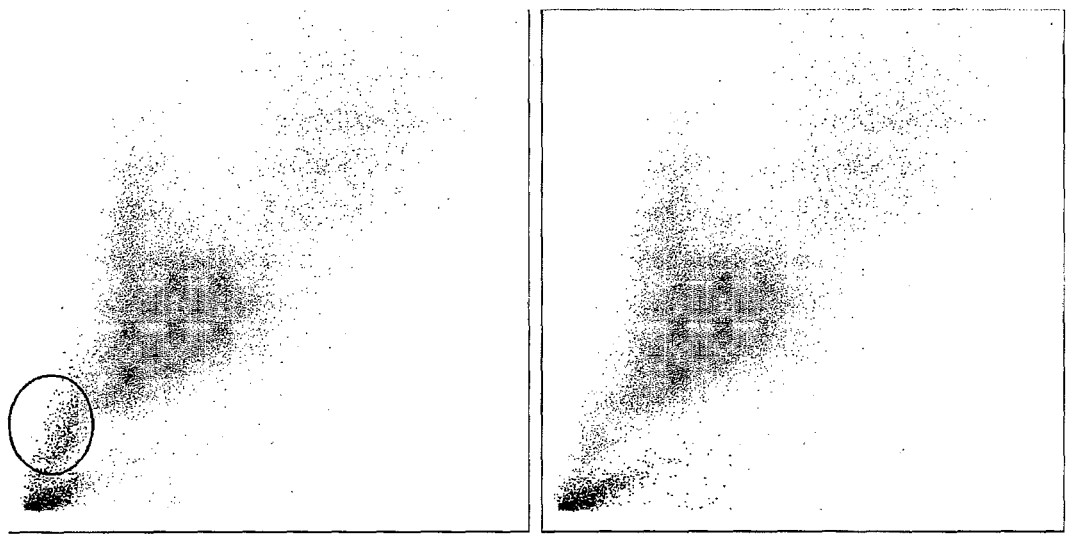
FIGS. 21A and 21B show a classification comparison for a case of microcytosis.

FIGS. 21A and 21B show a comparison of classifications for a case of microcytosis.

In a case of macroplatelets, this separation is found to be just as remarkable. Under such circumstances, 26% of platelets are macroplatelets that are identified as being erythrocytes when using resistive channel separation.

FIGS. 22A and 22B compare classifications for a case of macroplatelets.

The quality of the classification implemented using the invention is of clinical interest and makes it possible to diagnose β-thalassemia.

It is known that thalassemias are characterized by hypochromic microcyte anemia. It has been shown that the ratio between the percentage of microcytes over the percentage of hypochromic cells is a reliable means for distinguishing between iron-deficiency anemia and β-thalassemia.

The invention also makes it possible to have access to platelet activation since mean platelet density (MPD) serves to determine the ratio of platelets that are activated, and thus potentially the risk of thrombosis.

Finally, the invention makes it possible to detect qualitative anomalies of platelets, in particular the presence of macroplatelets.

There follows a brief description of how white blood cells are classified using the invention.

FIG. 23 shows an RES×EXT matrix for analyzing white blood cells using gating to separate the population.

With the invention, 2D statistics are calculated in the RES×EXT plane or in the VOL×IDX plane for the points under consideration, in order to find a linear regression.

The slope of the trend line is extracted, and the plane is rotated in order to make this line horizontal.

One-dimensional (1D) statistics are then performed and the standard deviations of the Xs and the Ys give respectively a major axis and a minor axis of an ellipse via two parameters Xc and Yc that give the standard deviation axes.

Figure 24:
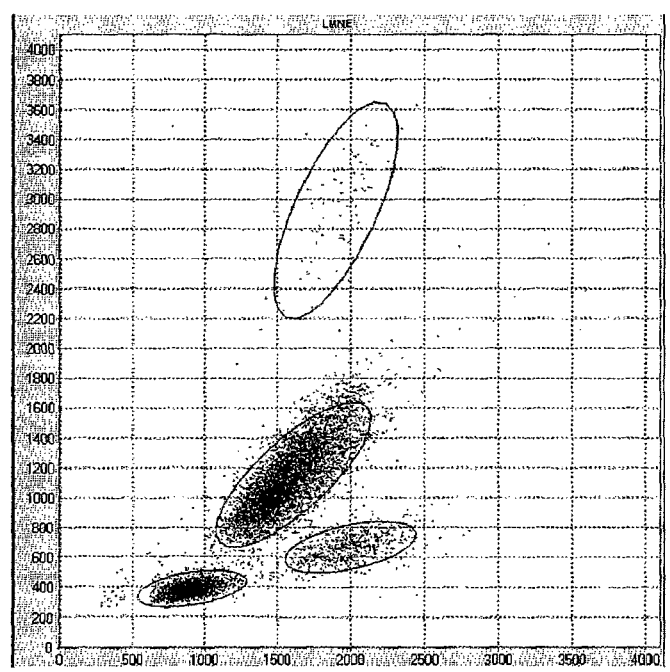
FIG. 24 shows an RES×EXT matrix for a population of white blood cells analyzing the 2D elliptical distributions of particles.

An ellipse (e.g. Xc, Yc) is obtained where the major axis is equal to Xc times the standard deviation of the Xs after rotation, and the minor axis is equal to Yc times the standard deviation of the Ys after rotation. In reality, these factors are adjusted automatically as a function of the number of events in the population under consideration, and as a function of the nature of the population. This type of ellipse is advantageously displayed on an RES×EXT matrix in the manner shown in FIG. 24, or on a VOL×IDX matrix.

In this figure, the neutrophils (NEU) are surrounded by an ellipse having major and minor axes at a ratio of 2.5. The lymphocytes are surrounded by an ellipse having major and minor axes at a ratio of 2.0 for up to 30 events, of 2.25 for 30 to 100 events, and of 2.5 for more than 100 events.

Figure 25A:
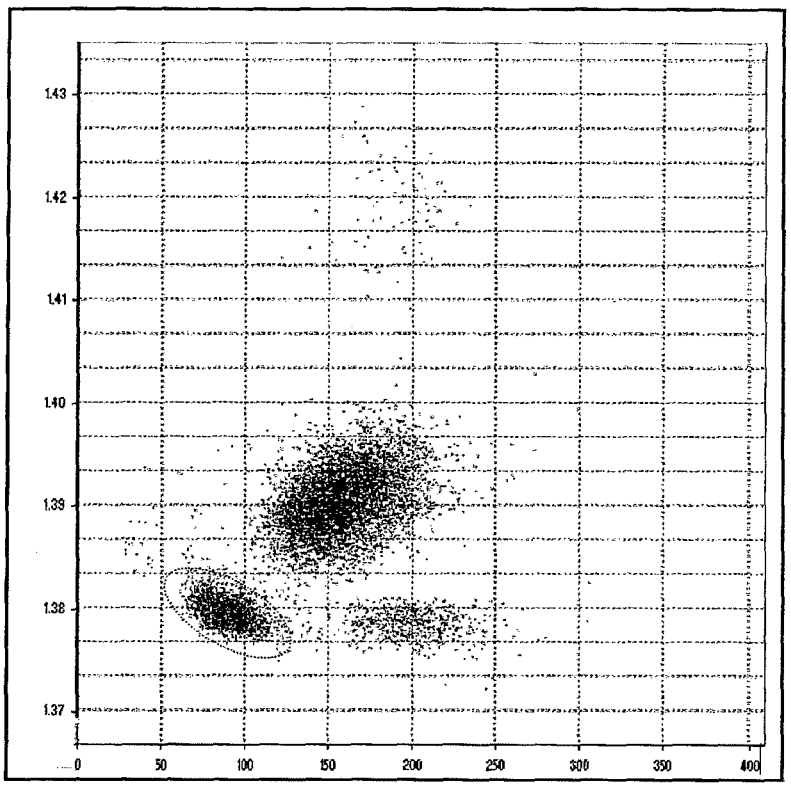
FIGS. 25A, 25B, and 25C show VOL×IDX matrices respectively for normal blood and for two kinds of pathological blood.
Figure 25B:
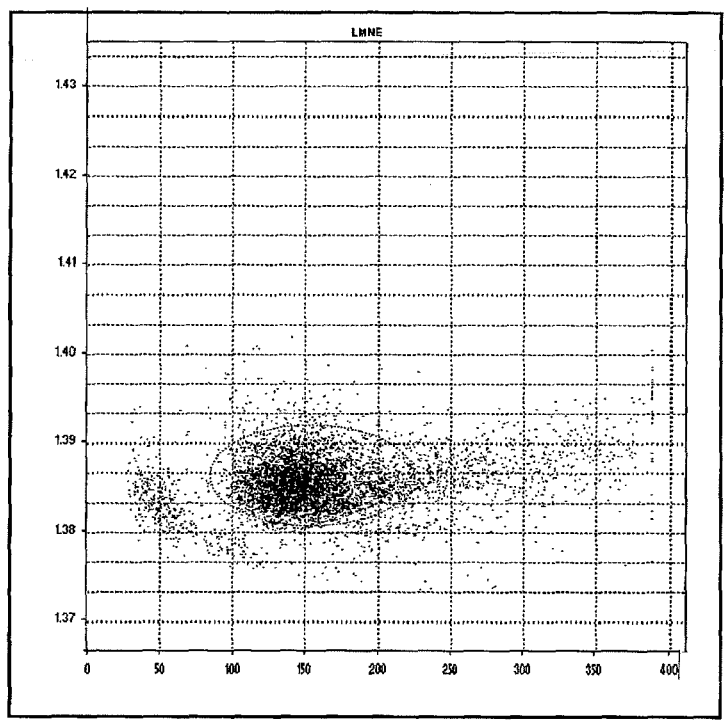
Figure 25C:
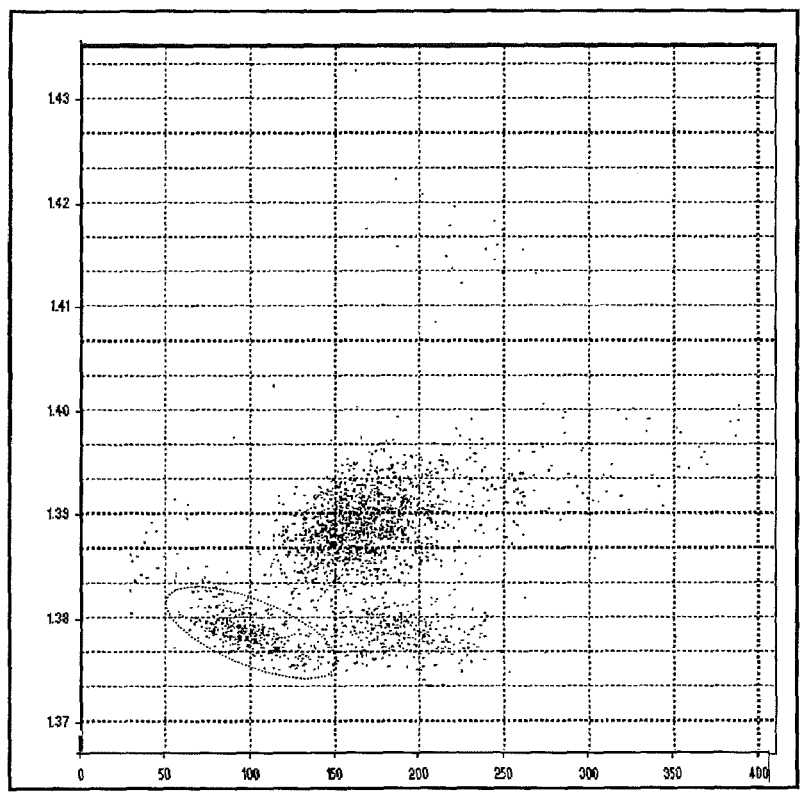

FIGS. 25A, 25B, and 25C show the VOL×IDX matrices on which ellipses can be drawn, respectively for normal blood and for two kinds of pathological blood.

Thus, on FIG. 25B, there can be observed the presence of immature granular neutrophils and of forms that are hyposegmented or degranulated. It can also be seen that the mean height of the neutrophils is less than that observed for normal blood: 1384 instead of 1391.

In FIG. 25C, it can be seen that the position of the lymphocytes is lower than for normal blood: 1378 instead of 1383.

Figure 26A:
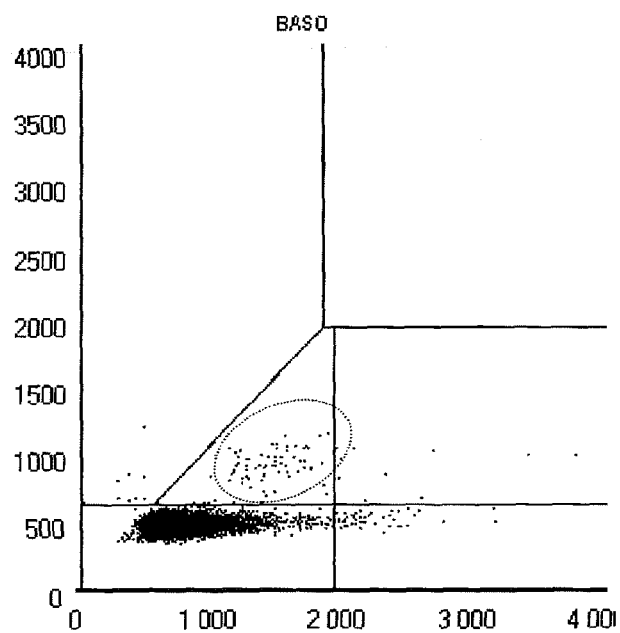
FIG. 26A shows an RES×EXT classification on a channel for discriminating basophils.
Figure 26B:
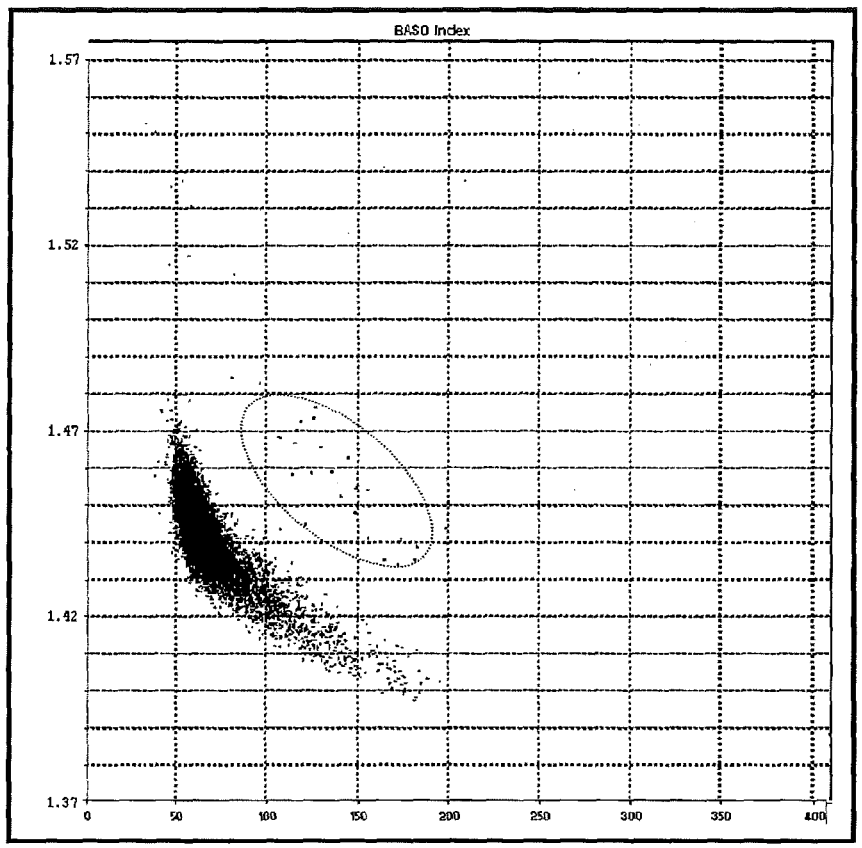
FIGS. 26B and 26C show respectively normal blood and lipid interference using the same channel in the VOL×IDX plane.
Figure 26C:
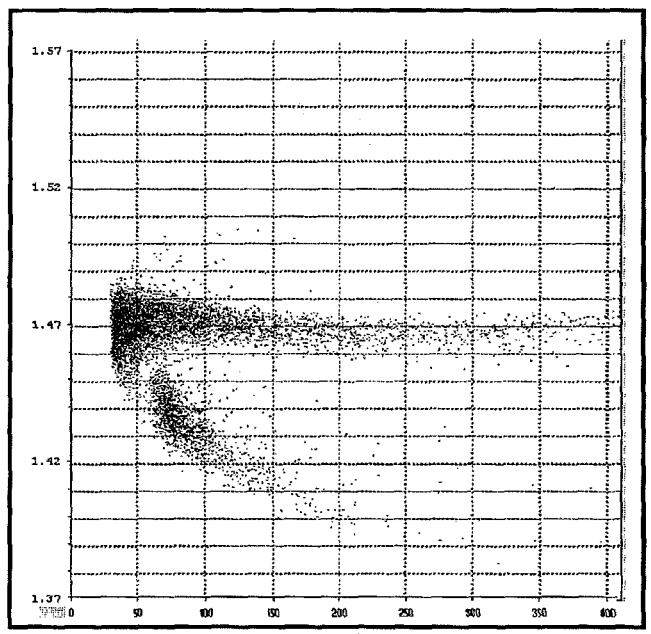

FIGS. 26A, 26B, and 26C show a classification of basophils obtained using another preparation and a reagent such as that described in patent FR 2 791 138.

FIG. 26A shows the classification in an RES×EXT plane in which the basophils are surrounded by an ellipse.

FIG. 26B shows the same blood but in the VOL-IDX plane. The cloud of points corresponding to the basophils is surrounded by an ellipse.

FIG. 26C shows the result of interference due to the presence of intra-lipids. An index distribution is observed having a peak at a value of about 1.47, which is a high value for leukocytes under the experimental conditions of the invention.

The invention thus makes it possible to distinguish between interferences above a refractive index of 1.46. In this high-index fraction, there is a continuum of volumes that is typical of an emulsion. That makes it possible to indicate that there is a problem in analyzing the sample.

Finally, it should be observed that various implementations can be performed on the principles of the invention.

Figure 27:
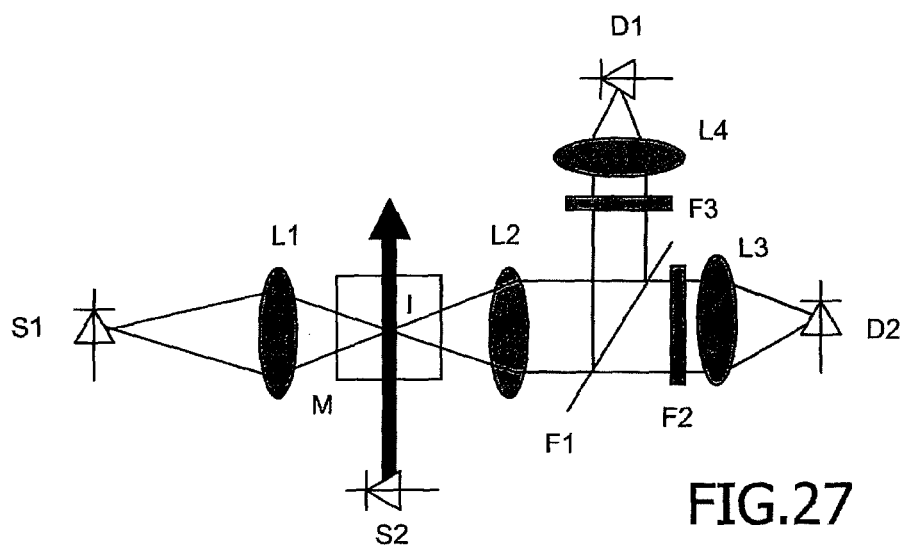
FIG. 27 shows a device for measuring the refringence of particles coupled with measuring fluorescence.

For example, the method of the invention for measuring the refringence of particles may be coupled with a measurement of fluorescence, as shown in FIG. 27. In such a set-up, the method of measuring the refringence of particles, based on measuring volume by an electric method and on measuring optical extinction in accordance with the invention is associated with measuring fluorescence. This measurement is made possible particle by particle by using a nucleic acid dye such as that contained in the "Fluowhite" or "Fluored" reagents (described in patents FR 2 821 428 and FR 2 759 166).

In those patents, mention is made of thiazole orange as means for marking nucleic acid. Thus, in the FIG. 27 device, a first light source S1, such as an LED is arranged so as to illuminate a stream of particles passing out from the plane of FIG. 27 at the point I within a measurement chamber M. A second measurement beam is also focused on the point I, which beam comes from a second light source S2, such that the beams coming from S1 and S2 meet at the point I, each emerging via a respective face of the measurement chamber M.

By way of example, this lighting arrangement is described by the Applicant in patent application FR 08/54229. It should be observed that the first light beam is shaped by a first optical combination of the L1 type to form a light beam presenting the illumination characteristics described in the present patent application, i.e. a light beam having a rectangular section of a×b with dimensions that continue to be equal to a=30 µm and b=90 µm, such that the aspect ratio, i.e. a/b, is equal to 1:3. The illumination wavelength is centered on $\lambda=650$ nm for a spectrum width of $\delta\lambda=30$ nm, giving the system a coherence length Lc of about $\lambda/\delta\lambda \approx 15$ µm. The numerical aperture is NA1=NA2=0.3. In this example, attention is directed to a second light source S2 constituted by a semiconductor laser diode emitting substantially monochromatic light centered on the wavelength of 488 nm. There follows a description of the configuration of the detection system coupled to the measurement chamber and operating under such conditions of illumination.

The detection system is coupled to the measurement chamber in the direction of the light source having lower coherence, i.e. S1. It is therefore coupled at ninety degrees to the source having greater coherence, i.e. S2. The light resulting from interaction between the microparticle and the illuminating beams is collected by a single receiver optical system, referenced L2, focused on I, i.e. the light beam from the point I is made parallel by the optic system F2.

The light beam has various spectral components that are analyzed by a set of filters F1, F2, and F3 so as to distinguish in this particular configuration between firstly the light on which the extinction measurement is performed and secondly the light due to fluorescence.

In the particular situation in which the nucleic acids have previously been marked by the thiazole orange molecule, as described in patent FR 2 759 166, the filter F1 is a dichroic type filter that reflects all spectral components of less than 580 nm through ninety degrees relative to the incident beam, and that transmits the spectral components greater than 580 nm.

The filters F2 and F3 are bandpass type filters that serve to optimize the rejection of spectral components that are not desired at the detectors D1 and D2. Specifically, the detector D1 must be sensitive only to the spectral components of the fluorescence of thiazole orange restricted to a spectrum and having a width of 50 nm and centered on 530 nm.

At D1, other wavelengths must be rejected by more than $10^5$, in particular for the wavelengths that come from the source S1 that fully illuminates the pupil of the receiver optical system L2.

F1, F2, and F3 are preferably multi-dielectric filters. Given the definition of the source S1, the filter F2 is naturally centered on the wavelength 650 nm with a passband of about 50 nm. Thus, in this particular set-up, it is possible to perform three physical measurements on each particle: an electrical measurement representative of the volume of the particle; an extinction measurement associated with the refringence of the particle; and also a fluorescence measurement associated with the nucleic acid content of the analyzed particle. By way of example, this set-up is particularly advantageous for measuring the refringence of the immature red blood cells known as reticulocytes.

Figure 28:
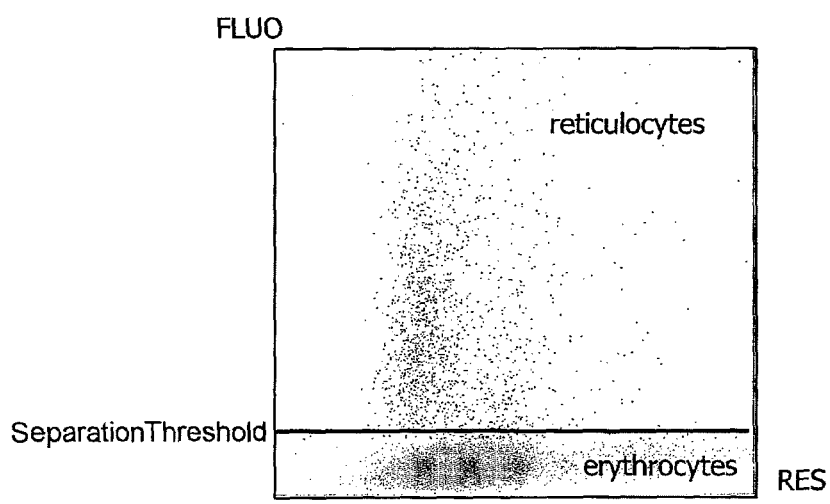
FIG. 28 shows an RES×FLUO matrix showing erythrocytes in pale gray and reticulocytes in black.

The fluorescence value makes it possible to separate erythrocytes, previously identified by erythrocyte/platelet separation, from reticulocytes, merely by using thresholding. If the fluorescence value exceeds the threshold, then the particles are reclassified as reticulocytes, as shown in FIG. 28.

The separation thresholds between erythrocytes and reticulocytes may be adjusted automatically by statistical analysis of the populations previously identified as erythrocytes. To do this, a fluorescence histogram is drawn up from which there are extracted the standard deviation written fSigma and the density maximum written fMode.

The following is then determined:

$$\text{SeparationThreshold}=f\text{Mode}+ fF1\text{SigmaCoef}*f\text{Sigma}=fF1\text{Offset}$$

where fF1SigmaCoef and fF1Offset are adjustable parameters.

Classification is then performed like that for the populations of erythrocytes in order to determine their refractive indices and then their corpuscular hemoglobin.

It is then possible to obtain a representation in the VOL× CHCr matrix of the reticulocytes, and thus to access the clinical parameter CHr=MRV×E(CHCr), FIG. 29B. MRV is the mean reticulocyte volume and E(CHCr) is the expectation of the CHCr distribution. Finally, since the extinction measurement needs to be performed in the red or the near infrared, it is possible to broaden the measurement band for fluorescence light. With an appropriate choice of fluorochromes, the person skilled in the art knows how to mark various particular compartments such as the membrane, the mitochondria, and the cytoplasm.

FIG. 30, in the EXT×FLUO plane, shows that it is possible to separate populations having different maturity levels by using fluorescence.

The fluorescence value makes it possible to distinguish between granulocytes, previously identified by the matrix of FIG. 23, and immature granulocytes, merely by using thresholding. If the fluorescence value exceeds the threshold, then the particles are reclassified as immature granulocytes, as shown in FIG. 30. With pathologies of the myeloid cell line (acute myeloid leukemia (AML), chronic myeloid leukemia (CML), myeloid proliferative syndrome (MPS), myeloid dysplastic syndrome (MDS)), the presence of immature granulocytes can falsify the measurement of the neutrophil index, the fluorescence measurement makes it possible to better identify the population of neutrophils on its own and thus guarantee that the refractive index measurement is performed on that population alone.

The fluorescence value serves to separate lymphocytes and monocytes, previously identified in the matrix of FIG. 23, from high RNA content (HRC) or immature cells, merely by using thresholding. If the fluorescence value exceeds the threshold, then the cells are reclassified as HRC cells, as shown in FIG. 30. With lymph-related pathologies (acute lymphoblastic leukemia (ALL), chronic lympocytic leukemia (CLL)) measuring fluorescence makes it possible to better identify the population of normal lymphocytes on its own and thus to guarantee that the refractive index measurement is performed on that population alone.

Another type of marking may consist in using monoclonal antibodies coupled to fluorescent compounds. The multiple fluorescences that come from fluorescent compounds can be analyzed by a multichannel detector, where each channel provides information about the intensity of the fluorescence of each fluorescent compound. The person skilled in the art knows that processing such fluorescences enables certain populations of cells to be better identified. Such multiple fluorescence measurements can be found to be particularly advantageous with leukocytes for which the effective refractive index can be measured together with its phenotype, e.g. plasmocytes detected by the CD45, CD38, and CD138 phenotype using the method of patent FR 2 895 087.

The invention claimed is:

1. A method of classifying and of flow measuring the refringence of at least two populations of particles present in a fluid by using a light source of short coherence time, of coherence length Lc<100 μm, used under extinction conditions at a center wavelength selected as a function of the range of volumes and the range of refractive indices expected for the particles under consideration, the method comprising the steps of:

using the light source to form a converging illuminating beam of aperture angle lying in the range 1° to 60°, selected as a function of the range of volumes and the range of refractive indices expected for the particles under consideration at the selected center wavelength and presenting lighting uniformity better than 10% in a rectangular volume measuring a×b×c, where a×b is the rectangular section of the beam having an aspect ratio a/b of less than 4, and where c is the depth of field defined as being the range of distances about the measurement point for which the power varies by no more than 10%, its value being situated at about 500 μm±250 μm;

causing the fluid with particles to flow through a measurement orifice;

measuring impedance vibrations (RES) as the particles go through the measurement orifice;

causing the fluid with particles to flow in the measurement window illuminated by the beam placed at the outlet from the measurement orifice;

measuring extinctions (EXT) on the axis of the beam as the particles pass through the measurement window, the measurement being performed by means of a device or a detector having a converging reception beam of aperture angle lying in the range 1° to 60° selected as a function of the range of volumes and the range of refractive indices expected for the particles under consideration;

merging the RES and EXT data to form events therefrom;

evaluating a relative refractive index IDX for each event; and classifying all of the events using at least one parameter selected from RES, EXT, and IDX.

2. A method according to claim 1, characterized in that the converging illuminating beam presents an aperture angle lying in the range 10° to 60°.

3. A method according to claim 1, characterized in that the relative refractive index is calculated using an expression of the type:

$$IDX = \frac{EXT - B \cdot \ln(RES + T) - D}{A \cdot \ln(RES + T) + C}$$

with A, B, C, D, and T being coefficients that depend on the measurement cycle.

4. A method according to claim 1, characterized in that the analyzed particles are cells in a biological liquid.

5. A method according to claim 1, characterized in that the wavelengths used for measuring particle refringence lie in the red and the near infrared beyond 0.6 μm.

6. A method according to claim 1, characterized in that the step of classifying events separates erythrocytes and platelets by using a wavelength lying in the range 600 nm to 800 nm and a numerical aperture NA1=NA2 lying in the range 0.2 to 0.6, including a step of separating erythrocytes and platelets as a function of default thresholds that define a belonging zone for platelets, the thresholds having values by default and being capable of being adjusted automatically.

7. A method according to claim 6, characterized in that the step of classifying events includes a sub-step of adjusting a resistive separation threshold between the particles for which extinction could not be measured, by determining a valley in a histogram prepared from all of the particles encountered.

8. A method according to claim 6, characterized in that the step of classifying events includes a sub-step of adjusting a resistive separation threshold calculated from statistical parameters, the mean and the standard deviation, of the particles encountered beneath a separation threshold defined by an affine straight line that is a function of the impedance and extinction measurements.

9. A method according to claim 6, characterized in that the step of classifying events includes a sub-step of adjusting a threshold defined by an affine straight line that is a function of the impedance and extinction measurements (RES, EXT) after rotating the entire impedance/extinction plane so as to place a separation line vertically by determining a valley in a histogram made from the abscissa axis points of events situated on either side of said separation line.

10. A method according to claim 6, characterized in that it includes a step of calculating the corpuscular hemoglobin concentrations of particles classified as being in the erythrocyte population with the help of an affine expression that is a function of their refractive indices IDX.

11. A method according to claim 10, characterized in that it includes a sub-classification step of classifying hypochromic, hyperchromic, and normochromic erythrocyte populations and microcyte, macrocyte, and normocyte erythrocyte populations.

12. A method according to claim 6, characterized in that it includes a step of calculating the densities of the particles classified in the platelet population using an affine expression that is a function of their refractive indices.

13. A method according to claim 12, characterized in that it includes a step of calculating the dry weights of platelets from their densities and from their volumes as known by the impedance measurements.

14. A method according to claim 6, characterized in that it includes a sub-classification step of classifying normal platelets, activated platelets, microplatelets, and macroplatelets.

15. A method according to claim 6, characterized in that the step of classifying events identified as erythrocytes separates erythrocytes from reticulocytes as a function of a threshold based on measuring fluorescence and corresponding to the erythrocyte maturity limit, the threshold having a default value that is suitable for being adjusted in automatic manner.

16. A method according to claim 6, characterized in that it includes a step of calculating the corpuscular hemoglobin concentrations of particles classified in the reticulocyte population by using an affine expression that is a function of refractive index.

17. A method according to claim 1, characterized in that the step of classifying events separates populations of leukocytes as constituted by lymphocytes, monocytes, granulocytes, neutrophils, and eosinophilic granulocytes, and comprises the steps of:
  a) using first 2D thresholding sub-step to separate background noise corresponding to the presence of debris, platelet aggregates, erythroblasts, artifacts, etc.; and
  b) using successive 2D thresholding sub-steps to separate the various populations and their atypical or immature sub-populations, and including:
    i) a sub-step of automatically adjusting a threshold between lymphocytes and neutrophilic granulocytes;
    ii) a sub-step of automatically adjusting a threshold between neutrophilic and eosinophilic granulocytes; and
    iii) a sub-step of automatically adjusting a threshold between monocytes and neutrophilic granulocytes.

18. A method according to claim 17, characterized in that it includes a step of calculating an activation index for particles classified as lymphocytes with the help of an affine expression that is a function of the calculated relative refractive index.

19. A method according to claim 17, characterized in that it includes a step of calculating an activation index for particles classified as lymphocytes by analyzing the 2D distribution of volumes and of optical extinctions, and by determining a statistical ellipse surrounding the population of lymphocytes, the ellipse being defined by the position of its center, by its major axis, by its minor axis, and by its angle.

20. A method according to claim 17, characterized in that it includes a step of calculating a lobularity/granularity index for the particles classified as neutrophilic granulocytes with the help of an affine expression that is a function of the calculated relative refractive index IDX.

21. A method according to claim 20, characterized in that the step of classifying events identified as neutrophilic or eosinophilic separates granulocytes and immature granulocytes as a function of a fluorescence measurement threshold that corresponds to the granulocyte maturity limit, the threshold having a value by default and being suitable for being adjusted in automatic manner.

22. A method according to claim 17, characterized in that it includes a step of calculating a lobularity/granularity index for the particles classified as neutrophilic granulocytes by analyzing the 2D distribution in impedance and extinction measurements or in volume and refractive index measurements (REX×EXT or VOL×IDX), and by determining a statistical ellipse surrounding the population of neutrophilic granulocytes, the ellipse being defined by the position of its center, by its major axis, by its minor axis, and by its angle.

23. A method according to claim 17, characterized in that the step of classifying events identified as lymphocytes or monocytes separates the lymphocytes or monocytes from the other particles having a high content of nucleic acid HRC as a function of a threshold for fluorescence measurements that corresponds to the maturity limit of mononuclear leukocytes, the threshold having a value by default and being suitable for being adjusted in automatic manner.

24. A method according to claim 1, characterized in that the step of classifying events separates basophilic granulocytes from other leukocyte populations and comprises the steps of:
  a) using 2D thresholding to separate the background noise corresponding to the presence of erythrocyte debris, platelet aggregates, erythroblasts, artifacts, etc.; and
  b) separating basophilic granulocytes from other leukocytes by 2D thresholding, including automatic adjustment of a threshold between the basophilic granulocytes and the other leukocytes.

25. A method according to claim 24, characterized in that it includes a step of detecting events presenting an abnormal relative refractive index and corresponding in fact to interference due to the presence of lipids, crystals, bubbles, etc.

26. A method according to claim 24, characterized in that it includes a step of detecting events having an abnormal relative refractive index and a volume distribution that is typical of an emulsion.

27. A method according to claim 1, characterized in that the method includes a step of illuminating the measurement volume with light at a wavelength that is selected to generate a fluorescence phenomenon, a step of measuring the fluorescence that is generated, and a step of classifying events after adjusting a fluorescence separation threshold.

* * * * *